(12) United States Patent
Springer et al.

(10) Patent No.: US 6,916,949 B2
(45) Date of Patent: Jul. 12, 2005

(54) METHODS OF CHEMICAL SYSTHESIS OF PHENOLIC NITROGEN MUSTARD PRODRUGS

(75) Inventors: Caroline Joy Springer, Sutton (GB); Dan Niculescu-Duvaz, Sutton (GB)

(73) Assignee: Cancer Research Technology Limited, London (GB)

(*) Notice: Subject to any disclaimer, the term of this patent is extended or adjusted under 35 U.S.C. 154(b) by 0 days.

(21) Appl. No.: 10/470,504
(22) PCT Filed: Jan. 24, 2002
(86) PCT No.: PCT/GB02/00281
§ 371 (c)(1),
(2), (4) Date: Jul. 29, 2003
(87) PCT Pub. No.: WO02/060862
PCT Pub. Date: Aug. 8, 2002

(65) Prior Publication Data
US 2004/0087813 A1 May 6, 2004

(30) Foreign Application Priority Data
Jan. 29, 2001 (GB) .............................................. 0102239

(51) Int. Cl.$^7$ .............................................. C07C 69/34
(52) U.S. Cl. ....................... 560/196; 560/155; 560/190; 562/590
(58) Field of Search ................................. 560/190, 193, 560/196, 156, 172, 192; 562/590, 596, 840, 872, 873, 874

(56) References Cited

U.S. PATENT DOCUMENTS 5,587,161 A * 12/1996 Burke et al. ............. 424/178.1
6,737,541 B2 * 5/2004 Siedlecki et al. ............. 560/19

FOREIGN PATENT DOCUMENTS

| WO | WO 94/02450 | 1/1994 |
| WO | 94/02450 A | 2/1994 |
| WO | WO 94/25429 | 11/1994 |
| WO | WO 96/03515 | 2/1996 |
| WO | 96/20169 A | 7/1996 |
| WO | WO 96/20169 | 7/1996 |
| WO | WO 98/51787 | 11/1998 |

OTHER PUBLICATIONS

Springer et al. J. Med. Chem. 1995, 38, 5051–5065.*
Blakey, D.C., et al., 1996, "ZD2767, an Improved System for Antibody-directed Enzyme Prodrug Therapy That Results in Tumor Regressions in Colorectal Tumor Xenografts," *Cancer Research*, vol. 56, pp. 3287–3292.
Corey, E.J., et al., 1972, "Protection of Hydroxyl Groups as tert-Butyldimethylsilyl Derivatives," *J. Am. Chem. soc.*, vol. 94, pp. 6190–6191.
Everett, J.L. and Ross, W.C.J., 1949, "420: Aryl-2-halogeno-alkylamines, Part II," *J. Chem. Soc.*, pp. 1972–1983.
Ferenz, C. R., et al., 1989, "Improved Conventional Synthesis for 14C-Labeled Polyglutamates of Folic Acid," *Journal of Labelled Compounds&Radiopharmaceuticals*, vol. 27, no. 7, pp. 737–751.
Greene, T.W., and Wuts, P.G.M., 1999, "Protection for Phenols and Catechols," *Protective Groups in Organic Chemistry*, 3rd Edition, pp. 246–292, published by John Wiley & Sons.
Greene, T.W., and Wuts, P.G.M., 1999, "Protection for the Hydroxyl Group, Including 1,2– and 1,3–Diols: Silyl Ethers," *Protective Groups in Organic Chemistry*, 3rd Edition, pp. 113–148, published by John Wiley & Sons.
Greene, T.W., and Wuts, P.G.M., 1999, "Protection for the Carboxyl Group: Ethers," in *Protective Groups in Organic Chemistry*, 3rd Edition, pp. 369–328, published by John Wiley & Sons.
Hagermann, H., 1983, Kohlensaure–derivative, in *Houben–Weyl Methoden der Organische Chemie: Kohlensäure Derivate* (editior: H Hagermann), vol. E4, 1395 pp., published by Georg Thieme Verlag (Stuttgart, New York).

(Continued)

Primary Examiner—Johann Richter
Assistant Examiner—Karl Puttlitz
(74) Attorney, Agent, or Firm—Nixon & Vanderhye P.C.

(57) ABSTRACT

This invention pertains to novel methods for the synthesis of certain nitrogen mustard prodrugs, such as N-{4-[N,N-bis(2-haloethylamino)-phenoxycarbonyl}-L-glutamic acid:

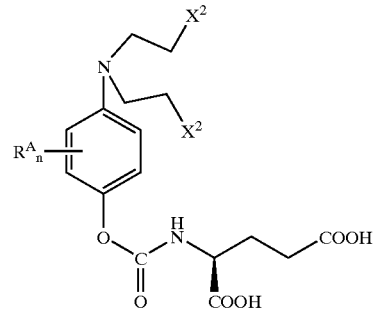

wherein: $X^2$ is a halo group, and is —F, —Cl, —Br, or —I; n is an integer from 0 to 4; and, each $R^A$ is an aryl substituent. The methods comprise, at least, the steps of: glutamate conjugation (GC); silyloxy deprotection (SD); and, sulfonic esterification (SU). Certain preferred methods comprise the steps of: amine substitution (AS); silyloxy protection (SP); phenolic deprotection (PD); activation (AC); glutamate conjugation (GC); silyloxy deprotection (SD); sulfonic estenfication (SU); halogenation (HL); glutamate deprotection (GD); and glutamic acid protection (GP).

54 Claims, No Drawings

OTHER PUBLICATIONS

Pawlenko, S., 1985, "e) Sulfonsäure–ester, el) sulfonsäure–organoester," in in *Houben–Weyl Methoden der Organische Chemie: Organische Schwefel–Verbindungen: Tiel 2* (editor: D Klamann), vol. E11, Part 2, pp. 1084–1094, published by Georg Thieme Verlag (Stuttgart, New York).

Lalonde et al., 1985, "Use of Organosilicon Reagents as Protective Groups in Organic Synthesis," *Synthesis*, 1985, pp. 817–845.

March, J., 1992, *Advanced Organic Chemistry*, 4th edition, "O–66: Formation of Alkyl Halides from Esters of Sulfuric and Sulfonic Acids, Halo–de–sulfonyloxy–substitution, etc.," p. 431, published by John Wiley & Sons (New York, USA).

Periasamy, M.P., et al., 1979, "Isocyanides in Organic Synthesis: A Review," *Org. Prep. Proceed. Int.*, vol. 11, No. 6, pp. 293–311.

Raucher, S., et al., 1985, "A Convenient Method for the Conversion of Amines to Carbamates," *Synthetic Communications*, vol. 15, No. 11, pp. 1025–1031.

Springer, C.J., et al., 1995, "Optimization of Alkylating Agent Prodrugs Derived from Phenol and Aniline Mustards: A New Clinical Candidate Prodrug (ZD2767) for Antibody–Directed Enzyme Prodrug Therapy (ADEPT)," *Journal of Medicinal Chemistry*, vol. 38, pp. 5051–5065.

Springer et al; "Optimization of Alkylating Agent Prodrugs Derived from Phenol and Aniline Mustards: A New Clinical Candidate Prodrug (ZD2767) for Antibody–Directed Enzyme Prodrug Therapy"; J. Med. Chem., 1995, vol. 38, no. 26, pp. 5051–5065m XO000986027.

* cited by examiner

METHODS OF CHEMICAL SYSTHESIS OF PHENOLIC NITROGEN MUSTARD PRODRUGS

This application is the US national phase of international application PCT/GB02/00281 filed 24 Jan. 2002, which designated in the US.

RELATED APPLICATION

This application is related to (and where permitted by law, claims priority to) United Kingdom patent application number GB 0102239.1 filed 29 Jan. 2001 the contents of which are incorporated herein by reference in their entirety.

TECHNICAL FIELD

This invention pertains generally to the field of organic chemical synthesis, and more particularly to novel methods for the synthesis of certain nitrogen mustard prodrugs, such as N-{4-[N,N-bis(2-haloethylamino)-phenoxycarbonyl}-L-glutamic acid, 12.

BACKGROUND

Peptidases are a class of enzymes (E) which act upon a substrate to cleave an amide linkage (—NH—C(=O)—) to give amino (—NH$_2$) and carboxylic acid (—C(=O)OH) products.

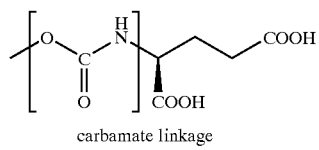

One peptidase of particular interest is carboxypeptidase G2 (referred to herein as "CPG2"). A preferred substrate for this enzyme is an L-glutamic acid group, inked to an aromatic ring via an amidic, carbamic, or ureidic linkage.

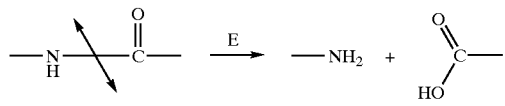

L-glutamic acid

However, glutamic acid analogs are also acceptable substrates. For example, L-glutamic acid modified at the γ-carbon (e.g., with an amide, —CONH$_2$, instead of an acid, —COOH) also serves as a suitable substrate for CPG2.

CPG2 is also tolerant as to whether the amide group is naked, or is part of a larger linkage, for example, a carbamate or a urea linkage.

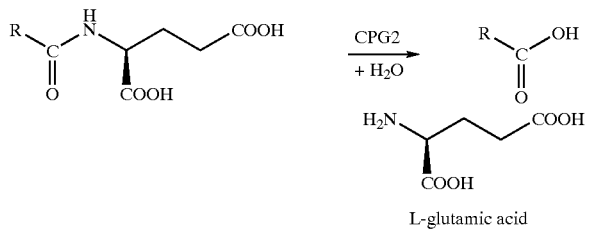

carbamate linkage urea linkage

For these compounds, CPG2 yields CO$_2$, L-glutamic acid, and R—ZH, wherein when Z is —O— (carbamates), R—ZH is a hydroxyl compound, R—OH, and when Z is —NH— (ureas), R—ZH is an amino compound, R—NH$_2$, where R is preferably an aromatic group.

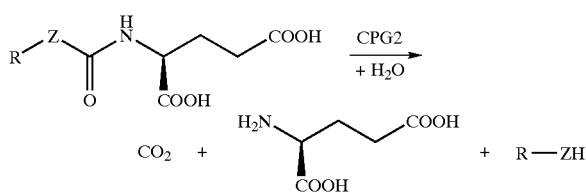

CPG2 and such substrates are useful in enzyme prodrug therapy (EPT) in which CPG2 may act upon a prodrug to yield an active compound. Examples of such therapies include antibody directed enzyme prodrug therapy (ADEPT), gene directed enzyme prodrug therapy (GDEPT), ligand directed enzyme prodrug therapy (LIDEPT), and bacteria directed enzyme prodrug therapy (BDEPT). See, for example, Burke, P. J., et al., 1994; Springer, C. J., et al., 1995; Blakey, D. C., et al., 1996; Springer, C. J., et al., 1996; Emery, S. C., et al., 1998.

In one class of therapy, CPG2 acts upon a prodrug to yield a phenolic nitrogen mustard compound which is useful, for example, in the treatment of a proliferative condition, for example, cancer.

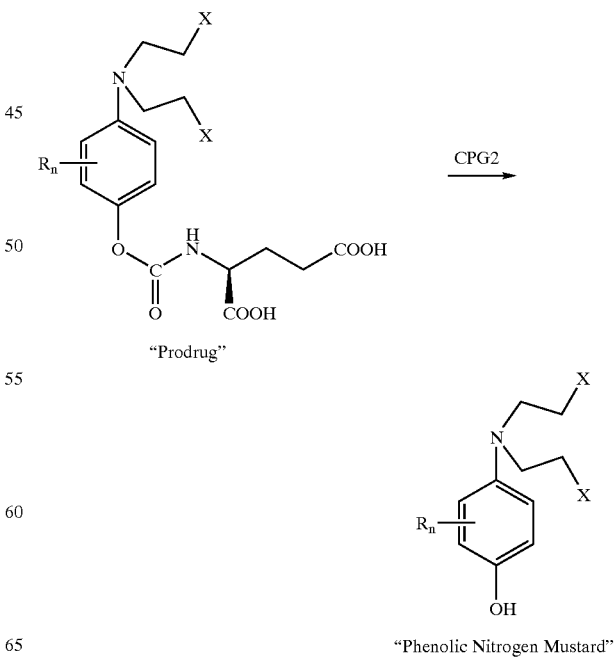

"Phenolic Nitrogen Mustard"

One method for the synthesis of such prodrug compounds is described in Burke, P. J., et al., 1994. An improved method was subsequently described in Heaton, D. W., et al., 1996 (see FIG. 2 therein) and is shown below:

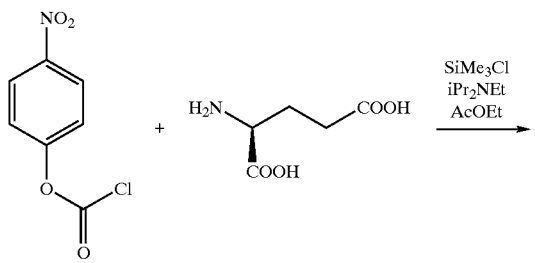

(I)

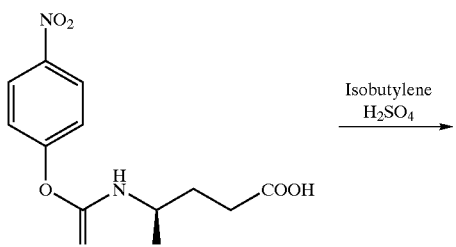

(II)

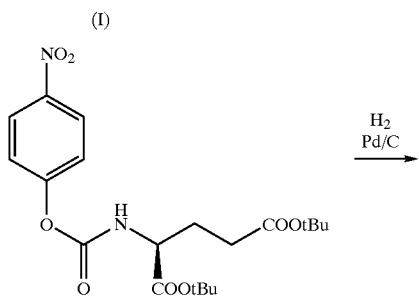

(III)

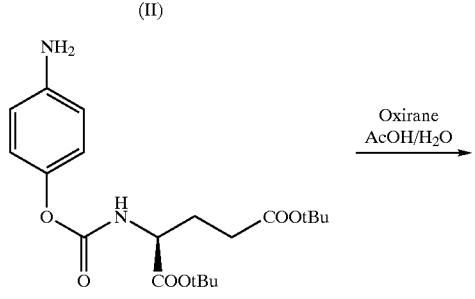

(IV)

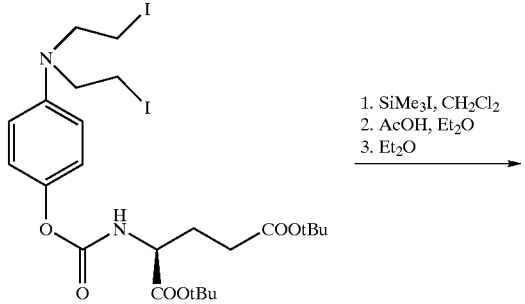

(V)

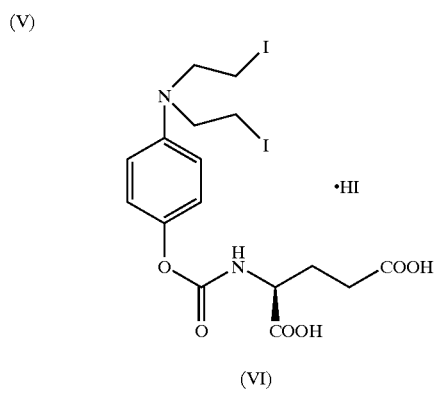

(VI)

This method suffers numerous disadvantages including several difficult and low yield reaction steps, such as:

(a) Step (I): 4-nitrophenyl chloroformate coupling (77% with respect to glutamic acid), (b) Step (III): reduction of nitroderivative to amine (58%); and, (c) Step (IV): hydroxyethylation, which is generally a difficult and low yield reaction (49%).

The present invention relates to new methods for the synthesis of such prodrug compounds, such as N-{4-[N,N-bis(2-haloethylamino)-phenoxycarbonyl}-L-glutamic acid. These new methods have one or more of the following advantages:

(1) higher yield of the desired prodrug with respect to the reagent, glutamic acid, than has been obtained in previous methods.

(2) higher yield of the glutamate conjugation reaction with respect to the precursors (e.g., 5+15 to give 6; 5A+15A to give 6A) than has been obtained in the corresponding conjugation reaction of previous methods (e.g., Step (I) above).

(3) amine substitution (e.g., 1 to 2; 1A to 2A) is performed earlier and with a cheaper reagent (e.g., 4-benzyloxyaniline, 1A) than in previous methods (e.g., the more expensive and advanced intermediate di-t-butyl, N-(4-amino-phenoxycarbonyl)-L-glutamate, in Step (IV) above).

(4) higher yield of amine substitution (e.g., 1 to 2; 1A to 2A) than has been obtained in the corresponding step in previous methods (e.g., Step (IV) above).

(5) simplified work-up of the product of amine substitution (e.g., 1 to 2; 1A to 2A) with respect to that in previous methods (e.g., Step (IV) above).

(6) introduction of the glutamic acid/glutamate residue at a later step (e.g., 5+15 to give 6; 5A+15A to give 6A) than in previous methods (e.g., Step (I) above), and thereby improving the economy of the overall process, in regard to this reagent.

SUMMARY OF INVENTION

One aspect of the invention pertains to a method of synthesis comprising the steps of, in order:

glutamate conjugation (GC), in which a 4-[N,N-bis(2-silyloxyethyl)amino]phenyl haloformate, activated carbonate, or activated carbamate 5, reacts with a glutamate, 15, to give an N-{4-[N,N-bis(2-silyloxyethyl) amino]phenoxycarbonyl}-L-glutamate, 6:

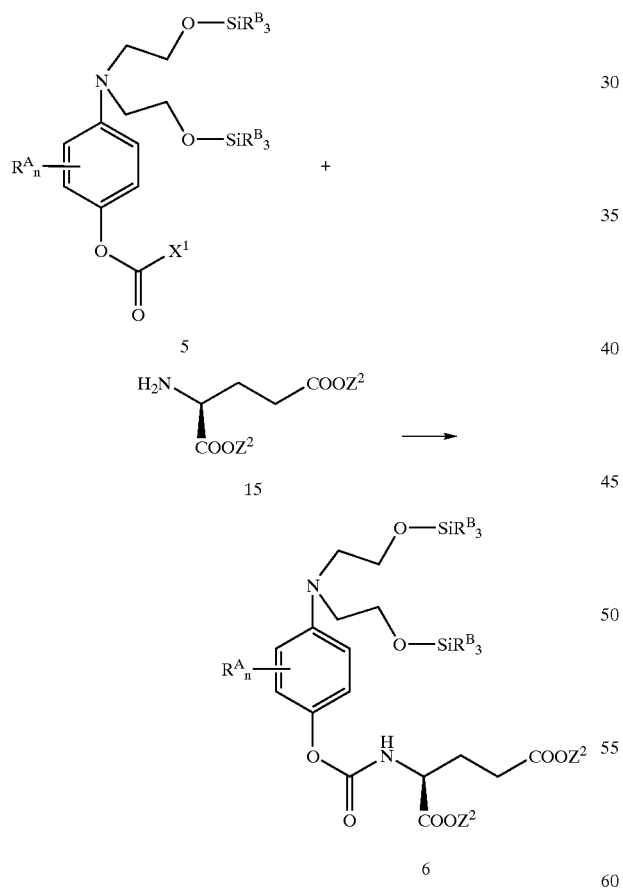

silyloxy deprotection (SD), in which said N-{4-[N,N-bis(2-silyloxyethyl)amino]phenoxy-carbonyl}-L-glutamate, 6, is converted to an N-{4-[N,N-bis(2-hydroxyethyl)amino]phenoxycarbonyl}-L-glutamate, 7:

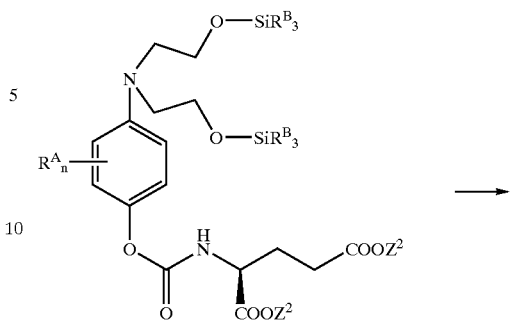

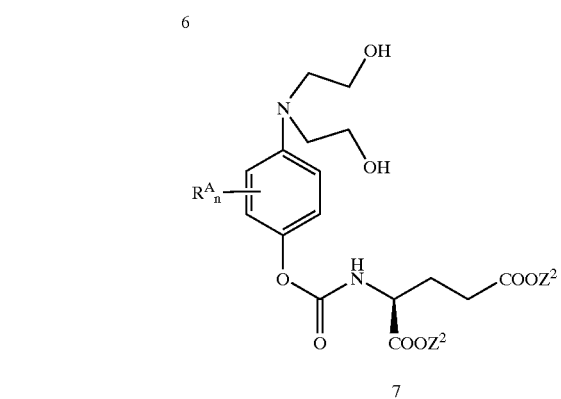

sulfonic esterification (SE), in which said N-{4-[N,N-bis(2-hydroxyethyl)amino]phenoxycarbonyl}-L-glutamate, 7, is converted to an N-(4-[N,N-bis(2-sulfonyloxyethyl)amino]phenoxycarbonyl}-L-glutamate, 8:

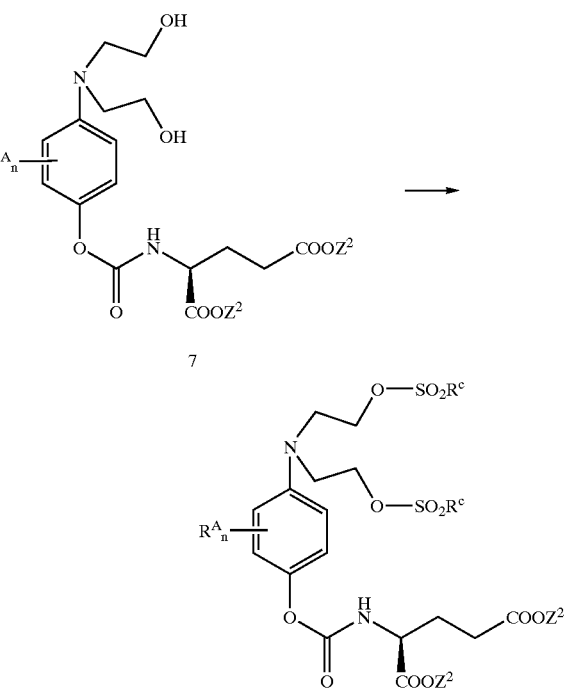

wherein:

X¹ is a leaving group;

n is an integer from 0 to 4;

each $R^A$ is independently an aryl substituent;

each $R^B$ is a silyl substituent, and is independently $C_{1-7}$alkyl, $C_{3-20}$heterocyclyl, or $C_{5-20}$aryl, and is optionally substituted;

each $R^C$ is a sulfonic substituent, and is independently $C_{1-7}$alkyl, $C_{3-20}$heterocyclyl, or $C_{5-20}$aryl, and is optionally substituted; and, each $Z^2$ is independently a carboxylic acid protecting group.

In one embodiment, the method further comprises, following the step of sulfonic esterification (SE), the additional step of:

halogenation (HL), in which said N-{4-[N,N-bis(2-sulfonyloxyethyl)amino]phenoxycarbonyl}-L-glutamate, 8, is converted to an N-{4-[N,N-bis(2-haloethyl)amino]phenoxycarbonyl}-L-glutamate, 9:

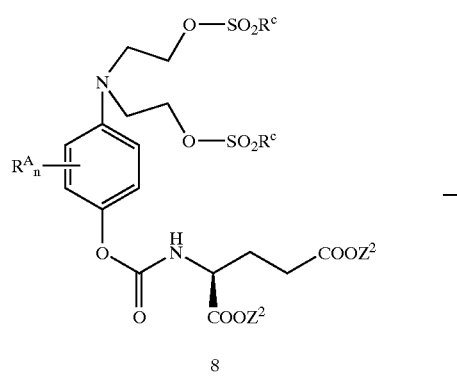

8

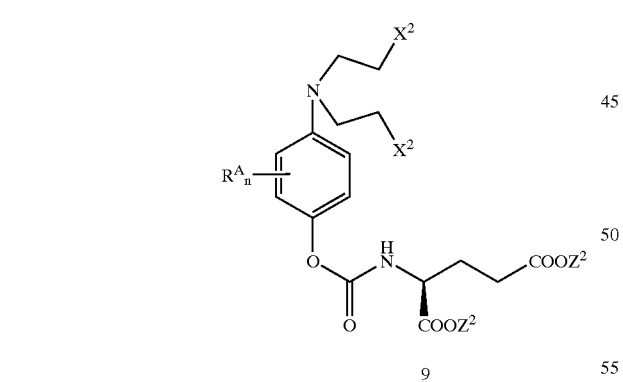

9 wherein each $X^2$ is independently —F, —Cl, —Br, —I.

In one embodiment, the method further comprises, following the step of sulfonic esterification (SE), the additional step of:

halogenation (HL), in which said N-{4-[N,N-bis(2-sulfonyloxyethyl)amino]phenoxycarbonyl}-L-glutamate, 8, is converted to an N-{4-[N-(2-sulfonyloxyethyl),N-(2-haloethyl)amino]phenoxycarbonyl}-L-glutamate, 10:

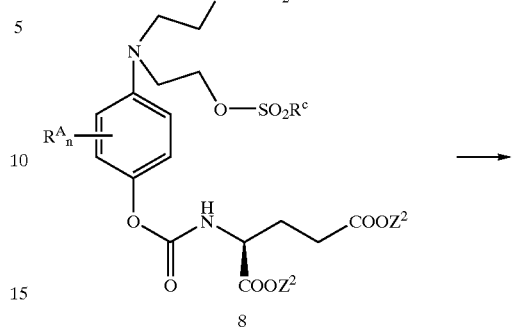

8

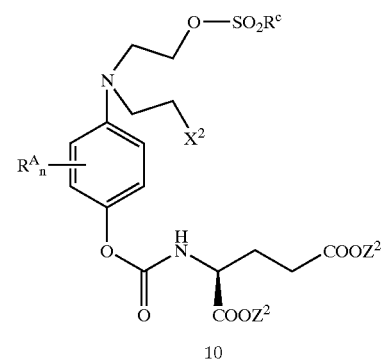

10 wherein each $X^2$ is independently —F, —Cl, —Br, —I.

In one embodiment, the method further comprises, following the step of sulfonic esterification (SE), the additional step of:

glutamate deprotection (GD), in which said N-{4-[N,N-bis(2-sulfonyloxyethyl)amino]phenoxycarbonyl}-L-glutamate, 8, is converted to an N-{4-[N,N-bis(2-sulfonyloxyethyl)amino]phenoxycarbonyl}L-glutamic acid, 11:

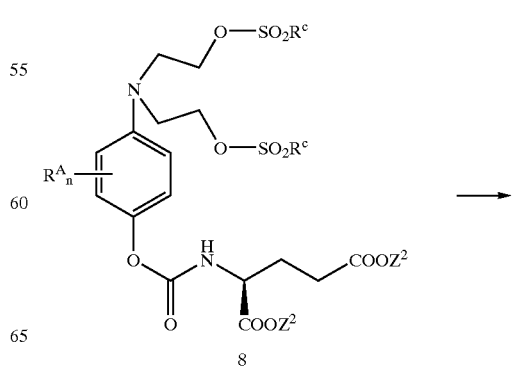

8

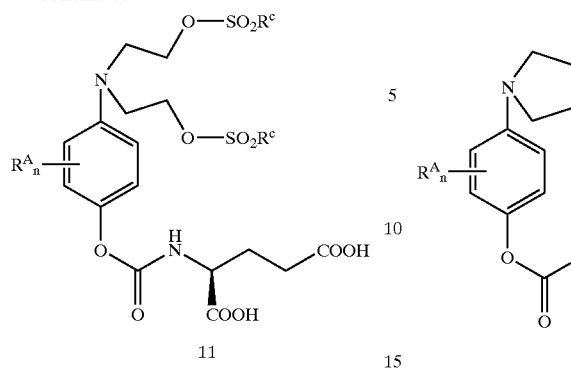

11

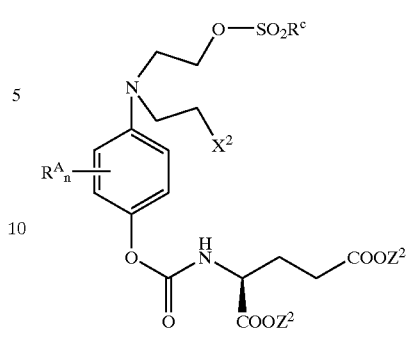

10

In one embodiment, the method further comprises, following the step of halogenation (HL), the additional step of:

glutamate deprotection (GD), in which said N-{4-[N,N-bis(2-haloethyl)amino]phenoxycarbonyl}-L-glutamate, 9, is converted to an N-{4-[N,N-bis(2-haloethyl)amino]phenoxycarbonyl}-L-glutamic acid, 12:

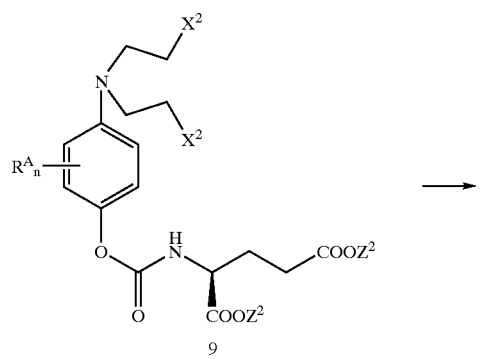

9

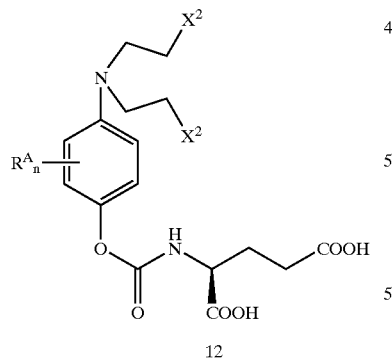

12

In one embodiment, the method further comprises, following the step of halogenation (HL), the additional step of:

glutamate deprotection (GD), in which said N-{4-[N-(2-sulfonyloxyethyl),N-(2-haloethyl)amino]phenoxycarbonyl}-L-glutamate, 10, is converted to an N-{4-[N-(2-sulfonyloxyethyl),N-(2-haloethyl)amino]phenoxycarbonyl}-L-glutamic acid, 13:

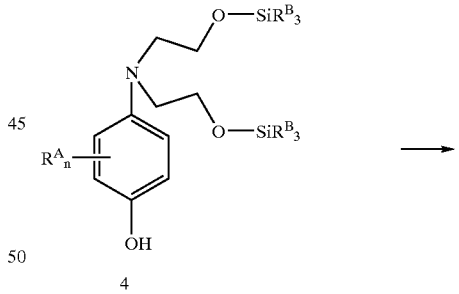

13

In one embodiment, the method further comprises, preceding the step of glutamate conjugation (GC), the additional step of:

activation (AC), in which a 4-[N,N-bis(2-silyloxyethyl)amino]phenol, 4, is converted to said 4-[N,N-bis(2-silyloxyethyl)amino]phenyl haloformate, activated carbonate, or activated carbamate 5:

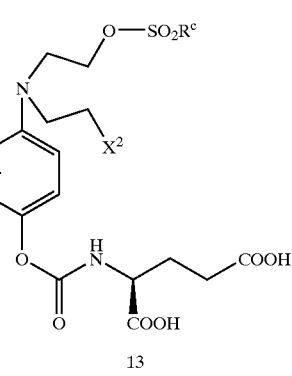

4

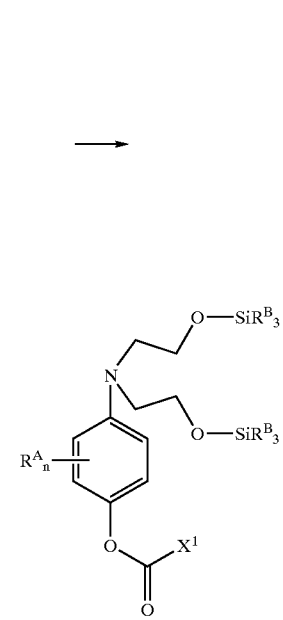

5

In one embodiment, the method further comprises, preceding the step of activation (AC), the additional steps of:

silyloxy protection (SP), in which a 4-(protected hydroxy)-N,N-bis(2-hydroxyethyl)aniline, 2, is converted to a 4-(protected hydroxy)-N,N-bis(2-silyloxyethyl) aniline, 3:

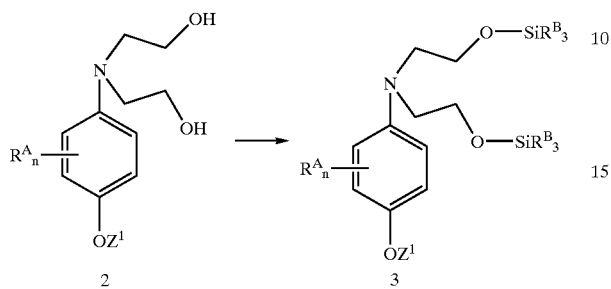

phenolic deprotection (PD), in which said 4-(protected hydroxy)-N,N-bis(2-silyloxyethyl)aniline, 3, is converted to said 4-[N,N-bis(2-silyloxyethyl)amino]phenol, 4:

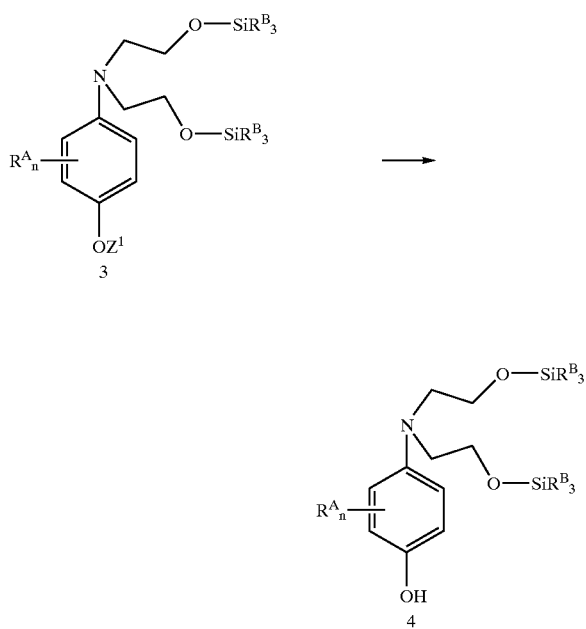

wherein $Z^1$ is a phenol protecting group.

In one embodiment, the method further comprises, preceding the step of silyloxy protection (SP), the additional step of:

amine substitution (AS), in which a 4-(protected hydroxy)-aniline, 1, is converted to said 4-(protected hydroxy)-N,N-bis(2-hydroxyethyl)aniline, 2:

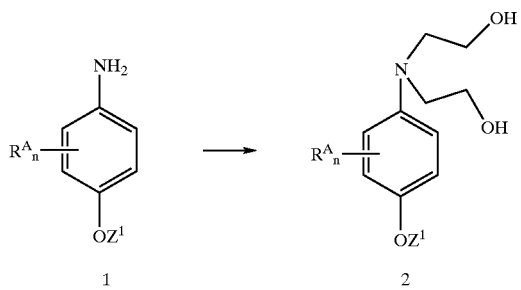

In one embodiment, the method further comprises, at any time preceding the step of glutamate conjugation (GC), the parallel step of:

glutamate protection (GP), in which L-glutamic acid, 14, is converted to said L-glutamate, 15:

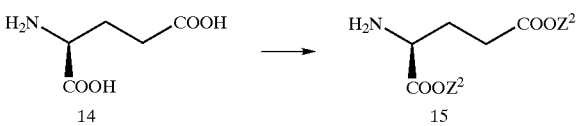

In one embodiment, said glutamate conjugation (GC) step is achieved by reaction in the presence of a base. In one embodiment, said glutamate conjugation (GC) step is achieved by reaction in the presence of the base triethylamine.

In one embodiment, said silyloxy deprotection (SD) step is achieved by reaction with triethylamine trihydrofluoride (NEt$_3$.3HF).

In one embodiment, said sulfonic esterification (SE) step is achieved by reaction with a sulfonic anhydride, (R$^C$SO$_2$)$_2$O. In one embodiment, said sulfonic esterification (SE) step is achieved by reaction with a sulfonic anhydride, (R$^C$SO$_2$)$_2$O, in the presence of a base. In one embodiment, said sulfonic esterification (SE) step is achieved by reaction with a sulfonic anhydride, (R$^C$SO$_2$)$_2$O, in the presence of one or both of triethylamine and 4-dimethylaminopyridine. In one embodiment, said sulfonic anhydride is methanesulfonic anhydride, (MeSO$_2$)$_2$O.

In one embodiment, said halogenation (HL) step is achieved by reaction with an alkaline halide. In one embodiment, said alkaline halide is sodium iodide.

In one embodiment, said glutamate deprotection (GD) step is achieved by reaction with acid. In one embodiment, said glutamate deprotection (GD) step is achieved by reaction with trifluoroacetic acid.

In one embodiment, said activation (AC) step is achieved by reaction with a carbonyl halide, $X^1C(=O)X^1$. In one embodiment, said activation (AC) step is achieved by reaction with a carbonyl halide, $X^1C(=O)X^1$ in the presence of a base. In one embodiment, said activation (AC) step is achieved by reaction with a carbonyl halide, $X^1C(=O)X^1$ in the presence of the base triethylamine. In one embodiment, said carbonyl halide is phosgene, ClC(=O)Cl.

In one embodiment, said silyloxy protection (SP) step is achieved by reaction with the corresponding halosilane, SiR$^B_3$X. In one embodiment, said silyloxy protection (SP) step is achieved by reaction with the corresponding chlorosilane, SiR$^B{}_3$Cl. In one embodiment, said silyloxy protection (SP) step is achieved by reaction with the corresponding halosilane, SiR$^B{}_3$X, in the presence of a base. In one embodiment, said silyloxy protection (SP) step is achieved by reaction with the corresponding halosilane, SiR$^B{}_3$X, in the presence of the base imidazole.

In one embodiment, said phenolic deprotection (PD) step is achieved by treatment with hydrogen gas and a palladium/carbon catalyst.

In one embodiment, said amine substitution (AS) step is achieved by treatment with ethylene oxide. In one embodiment, said amine substitution (AS) step is achieved by treatment with ethylene oxide in acetic acid, in the presence of a base. In one embodiment, said amine substitution (AS) step is achieved by treatment with ethylene oxide in acetic acid, in the presence of the base triethylamine.

In one embodiment, said glutamate protection (GP) step is achieved by reaction with isobutylene in the presence of sulfuric acid.

In one embodiment, X$^1$ is —F, —Cl, —Br, p-nitrophenoxy, pentafluorophenoxy, succinimidyloxy, or imidazolyl. In one embodiment, X$^1$ is —F, —Cl, or —Br. In one embodiment, X$^1$ is —Cl. In one embodiment, X$^1$ is p-nitrophenoxy, pentafluorophenoxy, succinimidyloxy. In one embodiment, X$^1$ is imidazolyl.

In one embodiment, each of R$^{A2}$, R$^{A3}$, R$^{A5}$, and R$^{A6}$ is independently —H or an aryl substituent selected from: halo; ether; thioether; acyl; ester; amido; disubstituted amino; cyano; nitro; and, C$_{1-7}$alkyl.

In one embodiment, each of R$^{A2}$, R$^{A3}$, R$^{A5}$, and R$^{A6}$ is independently —H, —F, —Cl, —CONH$_2$, —CN, or —Me.

In one embodiment, each of R$^{A2}$, R$^{A3}$, R$^{A5}$, and R$^{A6}$ is independently —H or —Me.

In one embodiment, n is 0 or each R$^A$ is —H.

In one embodiment, each RB is independently —Me, -Et, -nPr, -iPr, -nBu, -sBu, -iBu, -tBu, or -Ph. In one embodiment, each —SiR$^8{}_3$ group is independently —Si(Me)$_3$, —Si(Et)$_3$, —Si(iPr)$_3$, —Si(tBu)(Me)$_2$, or —Si(Ph)$_2$(tBu). In one embodiment, each —SiR$_{B3}$ group is —Si(tBu)(Me)$_2$.

In one embodiment, each R$^C$ is C$_{1-7}$alkyl or C$_{5-20}$aryl, and is optionally substituted. In one embodiment, each R$^C$ is —Me. In one embodiment, each R$^C$ is phenyl or substituted phenyl.

In one embodiment, each Z$^2$ is independently t-butyl, allyl, or benzyl. In one embodiment, each Z$^2$ is t-butyl.

In one embodiment, X$^2$ is —Cl, —Br, or —I. In one embodiment, X$^2$ is —Cl. In one embodiment, X$^2$ is —I.

In one embodiment, Z$^1$ is benzyl or allyl. In one embodiment, Z$^1$ is benzyl.

Another aspect of the present invention pertains to compounds obtainable by a method as described herein, or a method comprising a method as described herein. In one embodiment, the present invention pertains to a compound of the formula 11, 12, or 13 obtainable by a method comprising a method as described herein.

Another aspect of the present invention pertains to compounds obtained by a method as described herein, or a method comprising a method as described herein. In one embodiment, the present invention pertains to a compound of the formula 11, 12, or 13 obtained by a method comprising a method as described herein.

Another aspect of the present invention pertains to novel intermediates, as described herein, which are suitable for use in the methods of synthesis described herein. Examples of such intermediates include 3 (e.g., 3A), 4 (e.g., 4A), 5 (e.g., 5A), and 6 (e.g., 6A).

Another aspect of the present invention pertains to the use of such novel intermediates, as described herein, in the methods of synthesis described herein.

As will be appreciated by one of skill in the art, features and preferred embodiments of one aspect of the invention will also pertain to other aspect of the invention.

DETAILED DESCRIPTION OF THE INVENTION

The present invention pertains to new methods for the synthesis of compounds of the following formulae, and/or intermediates from which compounds of the following formulae may be prepared:

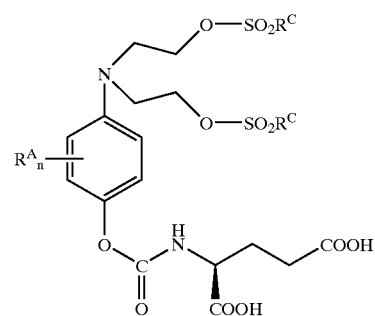

11

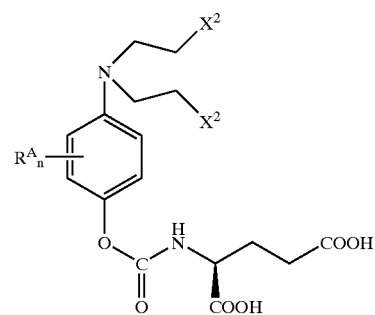

12

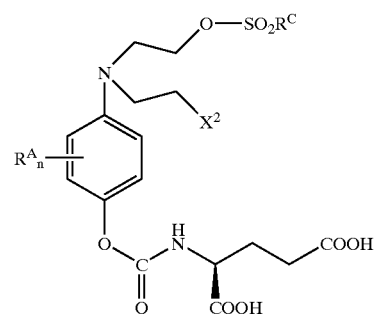

13 wherein:
  each X$^2$ is independently —F, —Cl, —Br, —I;
  n is an integer from 0 to 4;
  each R$^A$ is an aryl substituent; and,
  each R$^C$ is a sulfonic substituent, and is independently C$_{1-7}$alkyl, C$_{3-20}$heterocyclyl, or C$_{5-20}$aryl, and is optionally substituted.

(1) In one embodiment, the method comprises the steps of, in order:
  glutamate conjugation (GC);
  silyloxy deprotection (SD); and,
  sulfonic esterification (SU).

(2) In one embodiment, the method comprises the steps of, in order:
glutamate conjugation (GC);
silyloxy deprotection (SD);
sulfonic esterification (SU); and,
halogenation (HL).
method comprises the steps of, in order:
glutamate conjugation (GC);
silyloxy deprotection (SD);
sulfonic esterification (SU);
(3) In one embodiment, the and,
glutamate deprotection (GD).
(4) In one embodiment, the method comprises the steps of, in order:
glutamate conjugation (GC);
silyloxy deprotection (SD);
sulfonic esterification (SU);
halogenation (HL); and,
(5) In one embodiment, the method comprises the steps of, in order:
activation (AC);
glutamate conjugation (GC);
silyloxy deprotection (SD); and,
sulfonic esterification (SU).
(6) In one embodiment, the method comprises the steps of, in order:
activation (AC);
glutamate conjugation (GC);
silyloxy deprotection (SD);
sulfonic esterification (SU); and,
halogenation (HL).
(7) In one embodiment, the method comprises the steps of, in order:
activation (AC);
glutamate conjugation (GC);
silyloxy deprotection (SD);
sulfonic esterification (SU); and,
glutamate deprotection (GD).
(8) In one embodiment, the method comprises the steps of, in order:
activation (AC);
glutamate conjugation (GC);
silyloxy deprotection (SD);
sulfonic esterification (SU);
halogenation (HL); and,
glutamate deprotection (GD).
(9) In one embodiment, the method comprises the steps of, in order:
silyloxy protection (SP);
phenolic deprotection (PD);
activation (AC);
glutamate conjugation (GC);
silyloxy deprotection (SD); and,
sulfonic esterification (SU).
(10) In one embodiment, the method comprises the steps of, in order:
silyloxy protection (SP);
phenolic deprotection (PD);
activation (AC);
glutamate conjugation (GC);
silyloxy deprotection (SD);
sulfonic esterification (SU); and,
halogenation (HL).
(11) In one embodiment, the method comprises the steps of, in order:
silyloxy protection (SP);
phenolic deprotection (PD);
activation (AC);
glutamate conjugation (GC);
silyloxy deprotection (SD);
sulfonic esterification (SU); and,
glutamate deprotection (GD).
(12) In one embodiment, the method comprises the steps of, in order:
silyloxy protection (SP);
phenolic deprotection (PD);
activation (AC);
glutamate conjugation (GC);
silyloxy deprotection (SD);
sulfonic esterification (SU);
halogenation (HL); and,
glutamate deprotection (GD).
(13) In one embodiment, the method comprises the steps of, in order:
amine substitution (AS);
silyloxy protection (SP);
phenolic deprotection (PD);
activation (AC);
glutamate conjugation (GC);
silyloxy deprotection (SD); and,
sulfonic esterification (SU).
(14) In one embodiment, the method comprises the steps of, in order:
amine substitution (AS);
silyloxy protection (SP);
phenolic deprotection (PD);
activation (AC);
glutamate conjugation (GC);
silyloxy deprotection (SD);
sulfonic esterification (SU); and,
halogenation (HL).
(15) In one embodiment, the method comprises the steps of, in order:
amine substitution (AS);
silyloxy protection (SP);
phenolic deprotection (PD);
activation (AC);
glutamate conjugation (GC);
silyloxy deprotection (SD);
sulfonic esterification (SU); and,
glutamate deprotection (GD).
(16) In one embodiment, the method comprises the steps of, in order:
amine substitution (AS);
silyloxy protection (SP);
phenolic deprotection (PD);
activation (AC);
glutamate conjugation (GC);
silyloxy deprotection (SD);

sulfonic esterification (SU);

halogenation (HL); and, glutamate deprotection (GD).

(17) In one embodiment, the method additionally comprises the parallel step of glutamate protection (GP), at a time before glutamate conjugation (GC).

Amine Substitution (AS)

In this step, a 4-(protected hydroxy)-aniline, 1, is converted to a 4-(protected hydroxy)-N,N-bis(2-hydroxyethyl) aniline, 2.

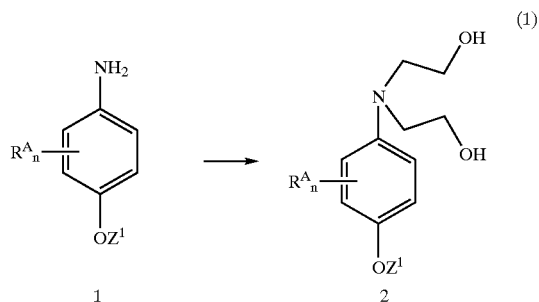

(1)

The group —$OZ^1$ is a protected hydroxy group. The group, —$Z^1$ is a suitable phenol protecting group. For a review of phenol protecting groups, see, for example, Greene et al., 1999a. in one preferred embodiment, the group, —$Z^1$, is allyl or benzyl. In one preferred embodiment, the group, —$Z^1$, is benzyl.

In one preferred embodiment, n is 0.

In one preferred embodiment, n is 0 or 1.

In one preferred embodiment, n is 0, 1, or 2.

In one preferred embodiment, n is 0, 1, 2, or 3.

In one preferred embodiment, n is 0, 1, 2, 3, or 4.

In one preferred embodiment, n is 1.

In one preferred embodiment, n is 1 or 2.

In one preferred embodiment, n is 1, 2, or 3.

In one preferred embodiment, n is 1, 2, 3, or 4.

In one preferred embodiment, n is 2.

In one preferred embodiment, n is 3.

In one preferred embodiment, n is 4.

In one preferred embodiment, the substituted phenylene group has the following formula:

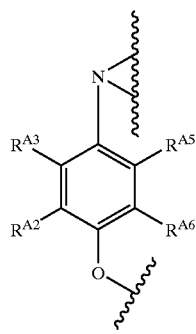

wherein each of $R^{A2}$, $R^{A3}$, $R^{A5}$, and $R^{A6}$ is independently —H or an aryl substituent.

In one preferred embodiment, each of $R^{A2}$, $R^{A3}$, $R^{A5}$, and $R^{A6}$ is —H.

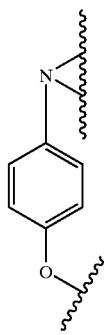

In one preferred embodiment, each of $R^{A2}$, $R^{A3}$, $R^{A5}$, and $R^{A6}$ is independently —H or an aryl substituent selected from: halo; ether (e.g., $C_{1-7}$alkoxy); acyl (e.g., $C_{1-7}$alkylacyl, $C_{5-20}$arylacyl); ester; acyloxy; amido; acylamido; thioamido; tetrazolyl; disubstituted amino; nitro; azido; cyano; cyanato; thiocyano; thioether (e.g., $C_{1-7}$alkylthio); sulfonate; sulfone; sulfonyloxy; sulfinyloxy; sulfonamino; sulfinamino; sulfamyl; sulfonamido; $C_{1-7}$alkyl (including, e.g., $C_{1-7}$haloalkyl, $C_{5-20}$aryl-$C_{1-7}$alkyl); $C_{3-20}$heterocyclyl; or $C_{5-20}$aryl (including, e.g., $C_{5-20}$carboaryl, $C_{5-20}$heteroaryl, $C_{1-7}$alkyl-$C_{5-20}$aryl and $C_{5-20}$haloaryl).

In one preferred embodiment, each of $R^{A2}$, $R^{A3}$, $R^{A5}$, and $R^{A6}$ is independently —H or an aryl substituent selected from:
—F, —Cl, —Br, and —I;
—OMe, —OEt, —O(tBu), and —$OCH_2Ph$;
—SMe, —SEt, —S(tBu), and —$SCH_2Ph$;
—C(=O)Me, —C(=O)Et, —C(=O)(tBu), and —C(=O)Ph;
—C(=O)OMe, —C(=O)OEt, and —C(=O)O(tBu);
—C(=O)$NH_2$, —C(=O)NHMe, —C(=O)$NMe_2$, and —C(=O)NHEt;
—NHC(=O)Me, —NHC(=O)Et, —NHC(=O)Ph, succinimidyl, and maleimidyl;
—CN;
—$NMe_2$, —$NEt_2$, —$N(iPr)_2$, —$N(nPr)_2$, —$N(nBu)_2$, and —$N(tBu)_2$;
—$NO_2$;
—$NMe_2$, —$NEt_2$, —$N(iPr)_2$, —$N(nPr)_2$, —$N(nBu)_2$, and —$N(tBu)_2$;
—Me, -Et, -nPr, -iPr, -nBu, -tBu;
—$CF_3$, —$CHF_2$, —$CH_2F$, —$CCl_3$, —$CBr_3$, —$CH_2CH_2F$, —$CH_2CHF_2$, and —$CH_2CF_3$;
—$OCF_3$, —$OCHF_2$, —$OCH_2F$, —$OCCl_3$, —$OCBr_3$, —$OCH_2CH_2F$, —$OCH_2CHF_2$, and —$OCH_2CF_3$;
—$CH_2CH_2NMe_2$; and,
optionally substituted phenyl.

In one preferred embodiment, each of $R^{A2}$, $R^{A3}$, $R^{A5}$, and $R^{A6}$ is independently —H or an aryl substituent selected from: halo; ether (e.g., $C_{1-7}$alkoxy); thioether; acyl; ester; amido; disubstituted amino; cyano; nitro; and, $C_{1-7}$alkyl (including, e.g., $C_{1-7}$haloalkyl, $C_{5-20}$aryl-$C_{1-7}$alkyl).

In one preferred embodiment, each of $R^{A2}$, $R^{A3}$, $R^{A5}$, and $R^{A6}$ is independently —H or an aryl substituent selected from:
—F, —Cl, —Br, and —I;
—OMe, —OEt, —O(tBu), and —$OCH_2Ph$;
—SMe, —SEt, —S(tBu), and —$SCH_2Ph$;
—C(=O)Me, —C(=O)Et, —C(=O)(tBu), and —C(=O)Ph;
—C(=O)OMe, —C(=O)OEt, and —C(=O)O(tBu);
—C(=O)$NH_2$, —C(=O)NHMe, —C(=O)$NMe_2$, and —C(=O)NHEt;

—NMe₂, —NEt₂, —N(iPr)₂, —N(nPr)₂, —N(nBu)₂, and —N(tBu)₂;
—CN;
—NO₂;
—Me, -Et, -nPr, -iPr, -nBu, -tBu;
—CF₃, —CHF₂, —CH₂F, —CCl₃, —CBr₃, —CH₂CH₂F, —CH₂CHF₂, and —N(tBu)₂;
—CH₂CH₂NMe₂.

In one preferred embodiment, each of $R^{A2}$, $R^{A3}$, $R^{A5}$, and $R^{A6}$ is independently —H or an aryl substituent selected from: —F, —Cl, —Br, —I, —OMe, —OEt, —SMe, —SEt, —C(=O)Me, —C(=O)OMe, —CONH₂, —CONHMe, —NMe₂, —NEt₂, —N(nPr)₂, —N(iPr)₂, —CN, —NO₂, —Me, -Et, —CF₃, —OCF₃, and -Ph.

In one preferred embodiment, each of $R^{A2}$, $R^{A3}$, $R^{A5}$, and $R^{A6}$ is independently —H or an aryl substituent selected from: —F, —Cl, —CONH₂, —CN, and —Me.

In one preferred embodiment, each of $R^{A2}$, $R^{A3}$, $R^{A5}$, and $R^{A6}$ is independently —H or —Me.

In one preferred embodiment, each of $R^{A2}$, $R^{A5}$, and $R^{A6}$ is —H, and $R^{A3}$ is as defined above.

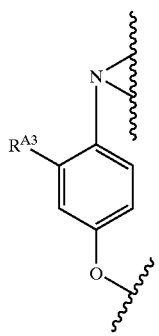

In one preferred embodiment, each of $R^{A2}$, $R^{A5}$, and $R^{A6}$ is —H, and $R^{A3}$ is —H, —F, —Cl, —CONH₂, —CN, or —Me.

In one preferred embodiment, each of $R^{A2}$, $R^{A5}$, and $R^{A6}$ is —H, and $R^{A3}$ is —H or —Me.

In one preferred embodiment, each of $R^{A2}$ and $R^{A5}$ is —H, and each of $R^{A3}$ and $R^{A5}$ is independently as defined above.

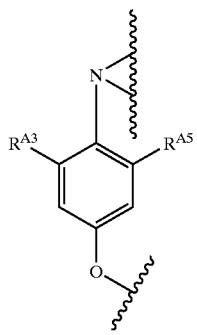

In one preferred embodiment, each of $R^{A2}$ and $R^{A6}$ is —H, and each of $R^{A3}$ and $R^{A5}$ is independently —H, —F, —Cl, —CONH₂, —CN, or —Me.

In one preferred embodiment, each of $R^{A2}$ and $R^{A6}$ is —H, and each of $R^{A3}$ and $R^{A5}$ is independently —H or —Me.

In one preferred embodiment, each of $R^{A5}$ and $R^{A6}$ is —H, and each of $R^{A2}$ and $R^{A3}$ is independently as defined above.

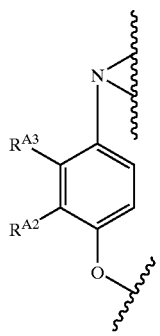

In one preferred embodiment, each of $R^{A5}$ and $R^{A6}$ is —H, and each of $R^{A2}$ and $R^{A3}$ is independently —H, —F, —Cl, —CONH₂, —CN, or —Me.

In one preferred embodiment, each of $R^{A5}$ and $R^{A6}$ is —H, and each of $R^{A2}$ and $R^{A3}$ is independently —H or —Me.

The conversion of the amino group, —NH₂, to a bis(2-hydroxyethyl)amino group, —N(CH₂CH₂OH)₂, may be achieved using well known methods. See, for example, Everett et al., 1949.

For example, the compound (or optionally an acid addition salt thereof) may be treated with ethylene oxide (oxirane), optionally in the presence of a suitable base, for example, triethylamine (NEt₃), and optionally in a suitable solvent.

Examples of suitable solvents include water, and protic and aprotic organic solvents. Examples of preferred solvents include acetic acid (MeCOOH, AcOH), alcohols, toluene, chloroform (CHCl₃), and benzene. In one preferred embodiment, the solvent is acetic acid.

In one embodiment, the molar ratio of the reagents ArNH₂.HCl:NEt₃:ethylene oxide is about 1:1–1.5:5–20. In one embodiment, the solvent is used in an amount of about 5–20 mL/mmol of ArNH₂. In one embodiment, the reaction time is about 3–120 h. In one embodiment, the reaction temperature is from about room temperature (e.g., about 20° C.) to about 230° C. In one embodiment, the reaction is carried out under stirring; a pressure vessel may be required if the reaction is carried out a temperature greater than about 40° C.

In one preferred embodiment, the molar ratio of the reagents ArNH2.HCl:NEt₃:ethylene oxide is about 1:1.1:10; the solvent is acetic acid; the solvent is used in an amount of about 10 mL/mmol of ArNH₂; the reaction time is about 72 h; and the reaction temperature is about room temperature; under stirring.

Silyloxy Protection (SP)

In this step, a 4-(protected hydroxy)-N,N-bis(2-hydroxyethyl)aniline, 2, is converted to a 4-(protected hydroxy)-N,N-bis(2-silyloxyethyl)aniline, 3.

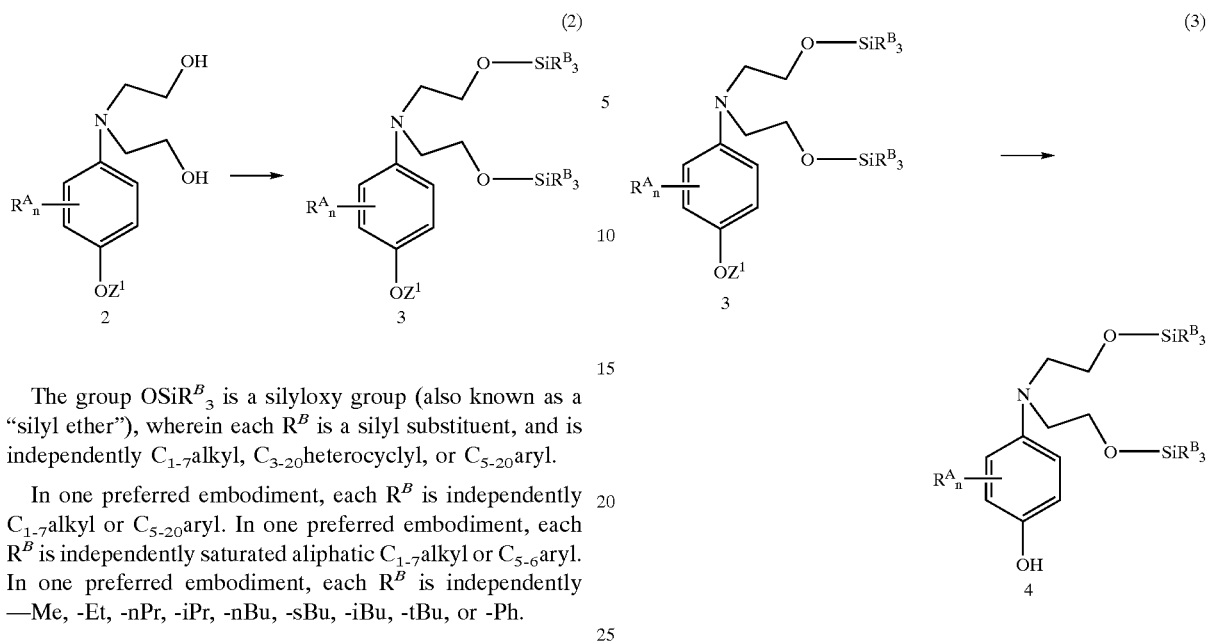

The group $OSiR^B_3$ is a silyloxy group (also known as a "silyl ether"), wherein each $R^B$ is a silyl substituent, and is independently $C_{1-7}$alkyl, $C_{3-20}$heterocyclyl, or $C_{5-20}$aryl.

In one preferred embodiment, each $R^B$ is independently $C_{1-7}$alkyl or $C_{5-20}$aryl. In one preferred embodiment, each $R^B$ is independently saturated aliphatic $C_{1-7}$alkyl or $C_{5-6}$aryl. In one preferred embodiment, each $R^B$ is independently —Me, -Et, -nPr, -iPr, -nBu, -sBu, -iBu, -tBu, or -Ph.

In one preferred embodiment, each group $—SiR_{B3}$ is independently —Si(Me)$_3$, —Si(Et)$_3$, —Si(iPr)$_3$, —Si(tBu)(Me)$_2$, or —Si(Ph)$_2$(tBu). In one preferred embodiment, both $—SiR^B_3$ groups are the same. In one preferred embodiment, each $—SiR^B_3$ group is —Si(tBu)(Me)$_2$.

The conversion of the hydroxyl groups, —OH, to silyloxy groups, $OSiR^B_3$, may be achieved using well known methods. See, for example, Lalonde et al., 1985 and Corey et al., 1972.

For example, in one method, the compound is reacted with the corresponding halosilane, $SiR^B_3X$, for example, the corresponding chlorosilane, $SiR^B_3Cl$, optionally in the presence of a suitable base, for example, imidazole, and optionally in a suitable solvent.

Examples of suitable solvents include dry aprotic organic solvents. In one preferred embodiment, the solvent is dimethylformamide (DMF).

In one embodiment, the molar ratio of the reagents diol (2):ClSi(t-Bu)(Me)$_2$:imidazole is about 1:2–5:4–10. In one embodiment, the solvent is used in an amount of about 3–10 mL/mmol of diol. In one embodiment, the reaction time is about 1–72 h. In one embodiment, the reaction temperature is about 0–100° C. In one embodiment, the reaction is carried out under stirring, under an inert gas (e.g., N$_2$, argon).

In one preferred embodiment, the molar ratio of the reagents diol (2):ClSi(t-Bu)(Me)$_2$:imidazole is about 1:2.5:4; the solvent is dimethylformamide; the solvent is used in an amount of about 3 ml/mmol of diol; the reaction time is about 18 h; the reaction temperature is about room temperature (e.g., about 20° C.); under stirring, under an inert gas.

Phenolic Deprotection (PD)

In this step, a 4-(protected hydroxy)-N,N-bis(2-silyloxyethyl)aniline, 3, is converted to a 4-[N,N-bis(2-silyloxyethyl)amino]phenol, 4.

The conversion of the protected phenolic hydroxyl group, $—OZ^1$, to a phenolic hydroxyl group, —OH, may be achieved using well known methods, and will vary according to the particular protecting group, $Z^1$, as discussed above.

For example, in one method, when $—OZ^1$ is a benzyloxy group, optionally substituted on the aromatic ring, the compound may be treated with hydrogen gas (H$_2$) and a palladium/carbon catalyst (Pd/C), optionally in a suitable solvent.

Examples of suitable solvents include protic and aprotic organic solvents. Examples of preferred solvents include tetrahydrofuran (THF), ethanol (EtOH), and ethyl acetate (AcOEt). In one preferred embodiment, the solvent is tetrahydrofuran. In one embodiment, the molar ratio of the reagents benzyl ether (3):Pd/C:H$_2$ is about 1:0.05–0.5 (active Pd):5–20. In one embodiment, the catalyst is Pd/C 5–30%. In one embodiment, the solvent is used in an amount of about 3–10 mL/mmol of benzyl ether. In one embodiment, the reaction time is about 1–48 h. In one embodiment, the reaction temperature is about 15–40° C. The reaction is carried out using hydrogenation apparatus; pressure may be applied if necessary.

In one preferred embodiment, the molar ratio of the reagents benzyl ether (3):Pd/C:H$_2$ is about 1:0.08 (active Pd):10; the catalyst is Pd/C 10%; the solvent is tetrahydrofuran; the solvent is used in an amount of about 5 mL/mmol of benzyl ether; the reaction time is about 24 h; the reaction temperature is about room temperature (e.g., about 20° C.); using hydrogenation apparatus.

Activation (AC)

In this step, a 4-[N,N-bis(2-silyloxyethyl)amino]phenol, 4, is converted to a 4-[N,N-bis(2-silyloxyethyl)amino] phenyl haloformate, activated carbonate, or activated carbamate 5.

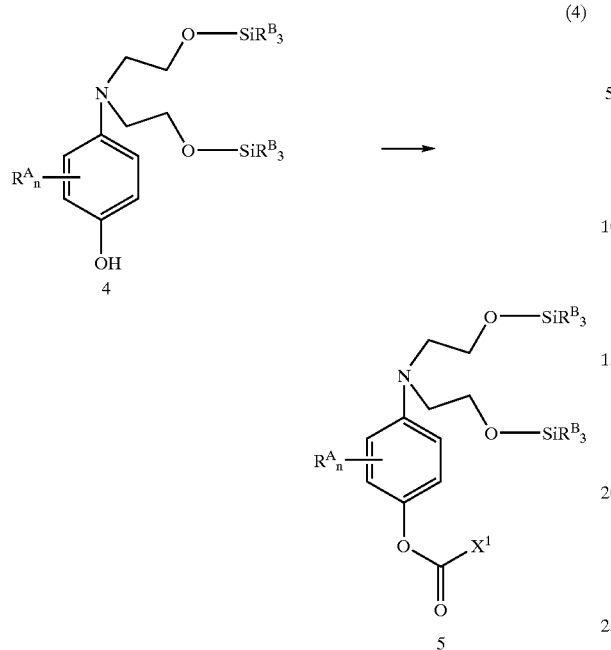

(4)

5

$X^1$ is a leaving group suitable for reaction with an amine to give a carbamate, as illustrated below,

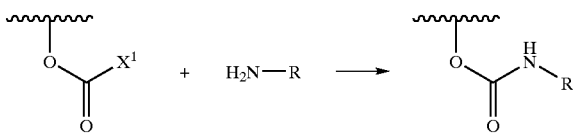

and as discussed below in the glutamate conjugation (GC) step, i.e., where 5+15 gives a conjugate, 6.

In one embodiment, the leaving group $X^1$ is (a) a halo group, and the group —OC(=O)$X^1$ is a haloformic ester group; (b) an activating group, —OR, and the group —OC(=O)$X^1$ is an activated carbonate; or (c) an activating group, —NR$_2$, and the group —OC(=O)$X^1$ is an activated carbamate.

In one preferred embodiment, the leaving group $X^1$ is a halo group, and the group —OC(=O)$X^1$ is a haloformic ester group. In one preferred embodiment, the leaving group $X^1$ is an activating group, —OR, and the leaving group —OC(=O)$X^1$ is an activated carbonate. In one preferred embodiment, the leaving group $X^1$ is an activating group, —NR$_2$, and the group —OC(=O)$X^1$ is an activated carbamate.

In one preferred embodiment, $X^1$ is —F, —Cl, —Br, p-nitrophenoxy, pentafluorophenoxy, succinimidyloxy, or imidazolyl.

In one preferred embodiment, $X^1$ is —F, —Cl, or —Br. In one preferred embodiment, $X^1$ is —Cl or —Br. In one preferred embodiment, $X^1$ is —F or —Cl. In one preferred embodiment, $X^1$ is —F. In one preferred embodiment, $X^1$ is —Cl. In one preferred embodiment, $X^1$ is —Br.

In one preferred embodiment, $X^1$ is p-nitrophenoxy, pentafluorophenoxy, or succinimidyloxy.

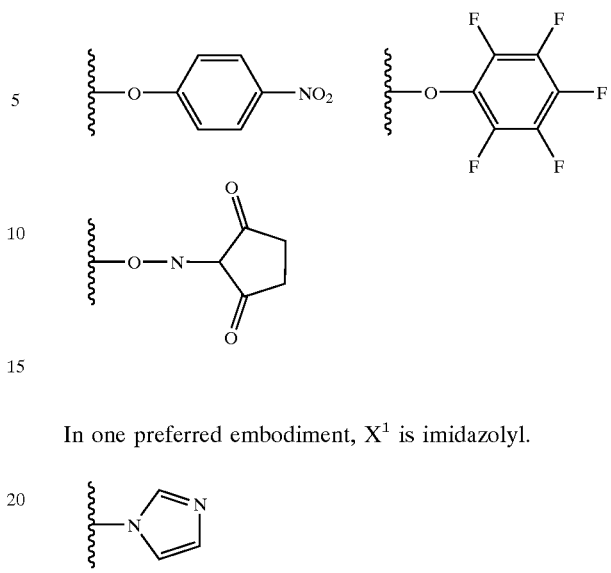

In one preferred embodiment, $X^1$ is imidazolyl.

The conversion of the phenolic hydroxyl group, —OH, to a haloformic ester, activated carbonate, or activated carbamate —O(C=O)$X^1$, may be achieved using well known methods. See, for example, Hagermann, 1983.

For example, in one method of converting to a haloformic ester, the compound is reacted with a carbonyl halide, $X^1$C(=O)$X^1$, for example, phosgene, ClC(=O)Cl, optionally in the presence of a suitable base (to combine with the HX$^1$, for example, HCl, formed during reaction), for example, triethylamine (NEt$_3$), and optionally in a suitable solvent.

Examples of suitable solvents include dry aprotic organic solvents. Examples of preferred solvents include tetrahydrofuran (THF) and toluene. In one preferred embodiment, the solvent is toluene.

In one embodiment, the molar ratio of the reagents phenol (4):COCl$_2$:NEt$_3$ is about 1:2–5:1–1.5. In one embodiment, the solvent is used in an amount of about 3–10 mL/mmol of phenol. In one embodiment, the reaction time is about 10 min to 24 h. In one embodiment, the reaction temperature is about 0–100° C. In one embodiment, the reaction is carried under stirring.

In one preferred embodiment, the molar ratio of the reagents phenol (4):COCl$_2$:NEt$_3$ is about 1:2.2:1.2; the solvent is toluene; the solvent is used in an amount of about 5 mL/mmol of phenol; the reaction time is about 10 min; the reaction temperature is about room temperature (e.g., about 20° C.); under stirring.

Glutamate Conjugation (GC)

In this step, a 4-[N,N-bis(2-silyloxyethyl)amino]phenyl haloformate, 5, reacts with a glutamate, 15, to give an N-{4-[N,N-bis(2-silyloxyethyl)amino]phenoxycarbonyl}-L-glutamate, 6.

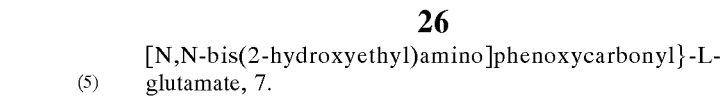

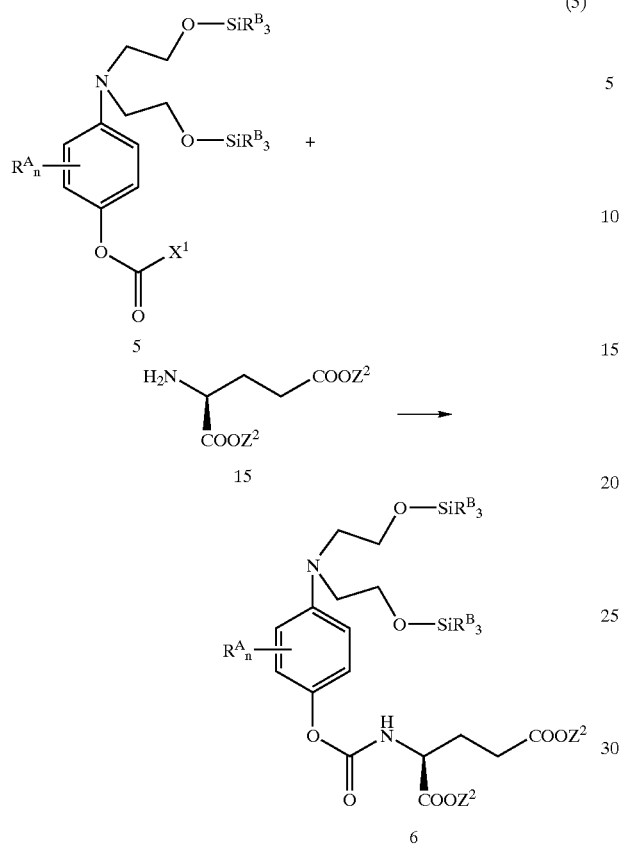

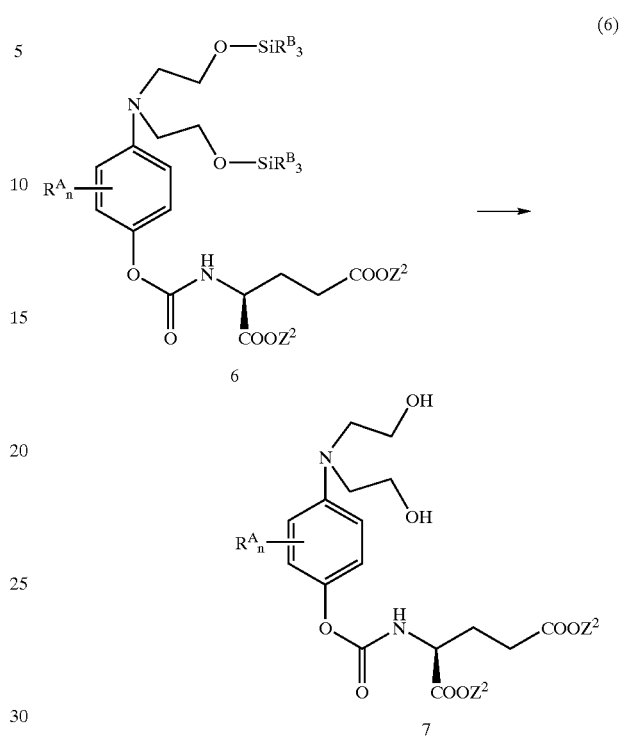

The formation of the carbamate linkage, —OC(=O)NH—, from the haloformic ester, —O(C=O)X$^1$, and the amino group, —NH$_2$ of the glutamate may be achieved using well known methods. See, for example, Periasamy et al., 1979 and Raucher et al., 1985.

For example, the two compounds may be mixed, optionally in the presence of a suitable base (to combine with the HX$^1$, for example, HCl, formed during reaction), for example, triethylamine (NEt$_3$), and optionally in a suitable solvent.

The glutamate, 15, may be provided in free form, or, more preferably, as an acid addition salt, e.g., 15.HCl.

Examples of suitable solvents include aprotic organic solvents. In one preferred embodiment, the solvent is tetrahydrofuran (THF), toluene, or dichloromethane (DCM, CH$_2$Cl$_2$). In one preferred embodiment, the solvent is tetrahydrofuran.

In one embodiment, the molar ratio of the reagents chloroformate (5):glutamate (15):NEt$_3$ is about 1:0.8–1.2:1–2. In one embodiment, the solvent is used in an amount of about 3–10 mL/mmol of chloroformate. In one embodiment, the reaction time is about 10 min to 24 h. In one embodiment, the reaction temperature is about 0–70° C. In one embodiment, the reaction is carried out under stirring.

In one preferred embodiment, the molar ratio of the reagents chloroformate (5):glutamate (15):NEt$_3$ is about 1:1:1.1; the solvent is tetrahydrofuran; the solvent is used in an amount of about 5 mL/mmol of chloroformate; the reaction time is about 10 min; the reaction temperature is about room temperature (e.g., about 20° C.); under stirring.

Siloxy Deprotection (SD)

In this step, an N-{4-[N,N-bis(2-silyloxyethyl)amino]phenoxycarbonyl}L-glutamate, 6, is converted to an N-{4-[N,N-bis(2-hydroxyethyl)amino]phenoxycarbonyl}-L-glutamate, 7.

The conversion of the silyloxy group, —OSiR$_3$, to a hydroxyl groups, —OH, may be achieved using well known methods. See, for example, Greene et al., 1999b.

For example, in one method, the compound is reacted with triethylamine trihydrofluoride (NEt$_3$.3HF), optionally in a suitable solvent.

Examples of suitable solvents include aprotic organic solvents. In one preferred embodiment, the solvent is tetrahydrofuran (THF), toluene, or dichloromethane (DCM, CH$_2$Cl$_2$). In one preferred embodiment, the solvent is tetrahydrofuran.

In one embodiment, the molar ratio of the reagents bis-silyl ether (6):NEt$_3$.3HF is about 1:5–20. In one embodiment, the solvent is used in an amount of about 5–20 mL/mmol of bis-silyl ether. In one embodiment, the reaction time is about 1–24 h. In one embodiment, the reaction temperature is about 0–40° C. In one embodiment, the reaction is carried out under stirring.

In one preferred embodiment, the molar ratio of the reagents bis-silyl ether (6):NEt$_3$.3HF is about 1:10; the solvent is tetrahydrofuran; the solvent is used in an amount of about 11 mL/mmol of bis-silyl ether; the reaction time is about 12 h; the reaction temperature is about room temperature (e.g., about 20° C.); under stirring.

Sulfonic Esterification (SU)

In this step, an N-{4-[N,N-bis(2-hydroxyethyl)amino]phenoxycarbonyl}-L-glutamate, 7, is converted to an N-{4-[N,N-bis(2-sulfonyloxyethyl)amino]phenoxycarbonyl}-L-glutamate, 8.

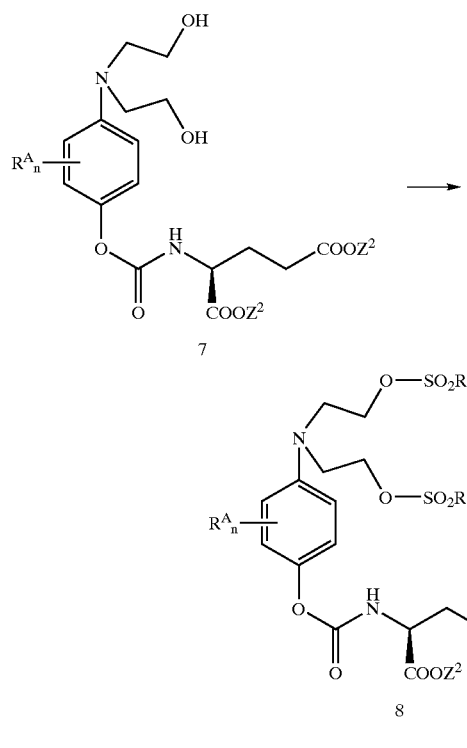

7

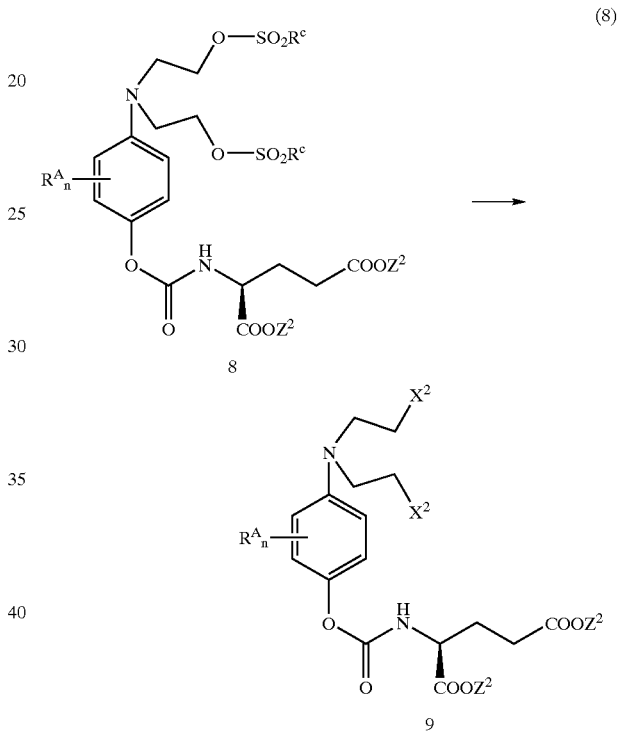

8

The $R^C$ group of the sulfonic ester, —OSO$_2$R$^C$, is $C_{1-7}$alkyl, $C_{3-20}$heterocyclyl, or $C_{5-20}$aryl, and is optionally substituted. In one preferred embodiment, $R^C$ is $C_{1-7}$alkyl or $C_{5-20}$aryl, and is optionally substituted.

In one preferred embodiment, $R^C$ is $C_{1-7}$alkyl, and is optionally substituted. In one preferred embodiment, $R^C$ is —Me, -Et, -nPr, -iPr, -nBu, -iBu, -sBu, or -tBu. In one preferred embodiment, $R^C$ is —Me (and the group —SO$_2$R$^C$ is mesyl).

In one preferred embodiment, $R^C$ is phenyl or substituted phenyl. In one preferred embodiment, $R^C$ is phenyl (and the group —SO$_2$R$^C$ is phenylsulfonyl). In one preferred embodiment, $R^C$ is para-methylphenyl (and the group —SO$_2$R$^C$ is tosyl). In one preferred embodiment, $R^C$ is para-bromophenyl (and the group —SO$_2$R$^C$ is brosyl). In one preferred embodiment, $R^C$ is para-nitrophenyl (and the group —SO$_2$R$^C$ is nosyl).

The conversion of the hydroxy groups, —OH, to sulfonic ester groups, —OSO$_2$R$^C$, may be achieved using well known methods. See, for example, Hagermann, 1985.

For example, in one method, the compound is reacted with sulfonic anhydride, (R$^C$SO$_2$)$_2$O, for example, methanesulfonic anhydride, (MeSO$_2$)$_2$O, optionally in the presence of one or more bases, for example, triethylamine (NEt$_3$) and/or 4-dimethylaminopyridine (DMAP), optionally in a suitable solvent.

Examples of suitable solvents include dry aprotic organic solvents. In one preferred embodiment, the solvent is dichloromethane (DCM, CH$_2$Cl$_2$), tetrahydrofuran (THF), ethyl acetate (AcOEt), or toluene. In one preferred embodiment, the solvent is dichloromethane.

In one embodiment, the molar ratio of the reagents diol (7):(MeSO$_2$)$_2$O:NEt$_3$:DMAP is about 1:2–10:2–10:0.05–2. In one embodiment, the solvent is used in an amount of about 3–20 mL/mmol of diol. In one embodiment, the reaction time is about 1–48 h. In one embodiment, the reaction temperature is about 0–50° C. In one embodiment, the reaction is carried out in an ice bath. In one embodiment, the reaction is carried out under stirring.

In one preferred embodiment, the molar ratio of the reagents diol (7):(MeSO$_2$)$_2$O:NEt$_3$:DMAP is about 1:4.3:5.4:0.07; the solvent is dichloromethane; the solvent is used in an amount of about 3 mL/mmol of diol; the reaction time is about 18 h; the reaction starts at 0° C. and is allowed to warm at room temperature; under stirring.

Halogenation (HL)

In this step, an N-{4-[N,N-bis(2-sulfonyloxyethyl)amino]phenoxycarbonyl}-L-glutamate, 8, is converted to either:

(a) a dihalo product, N-{4-[N,N-bis(2-haloethyl)amino]phenoxycarbonyl}-L-glutamate, 9.

or:

(b) a mixed halo-sulfonyl product, N-{4-[N-(2-sulfonyloxyethyl),N-(2-haloethyl)amino]phenoxycarbonyl}-L-glutamate, 10.

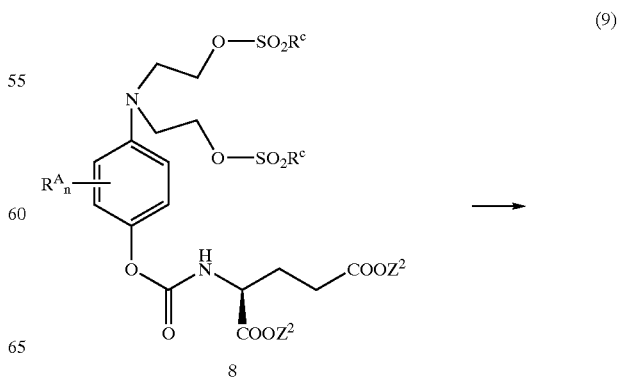

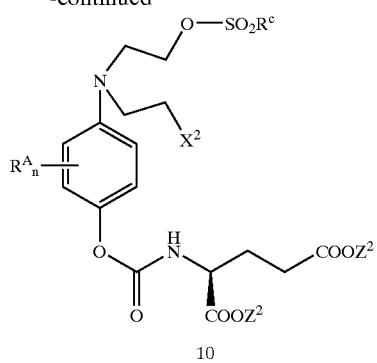

10

In one preferred embodiment, the reaction gives the dihalo product, 9.

Each group $X^2$ is independently —F, —Cl, —Br, —I. In one preferred embodiment, each $X^2$ is independently —Cl, —Br, or —I. In one preferred embodiment, each $X^2$ is independently —Cl or —I. In one preferred embodiment, each $X^2$ is independently —Cl or —Br. In one preferred embodiment, each $X^2$ is independently —Br or —I. In one preferred embodiment, each $X^2$ is —F. In one preferred embodiment, each $X^2$ is —Cl. In one preferred embodiment, each $X^2$ is —Br. In one preferred embodiment, each $X^2$ is —I. In one embodiment, when the product is a dihalo product, both $X^2$ groups are the same (e.g., difluoro, dichloro, dibromo, diiodo).

For the mixed halo-sulfonyl products, 10, a preferred sulfonyloxy group, —$OSO_2R^C$, is —$OSO_2Me$.

The conversion of the sulfonyloxy groups, —$OSO_2R^C$, to halo groups, —$X^2$, may be achieved using well known methods. See, for example, March, 1992.

For example, in one method, the compound is reacted with alkaline halide, for example, sodium halide, for example, sodium iodide, optionally in a suitable solvent.

Examples of suitable solvents include aprotic organic solvents. In one preferred embodiment, the solvent is tetrahydrofuran (THF), acetone, dimethylformamide (DMF), acetonitrile (ACN), or dimethylacetamide. In one preferred embodiment, the solvent is acetone.

Examples of suitable couples of alkaline halide/solvent include, for example, NaI/acetone, LiBr/tetrahydrofuran, and LiCl/dimethylacetamide. In one preferred embodiment, the alkaline halide/solvent couple is NaI/acetone.

In one embodiment, the molar ratio of the reagents mesylate (8):NaI is about 1:10–20. In one embodiment, the solvent is used in an amount of about 10–50 mL/mmol of mesylate. In one embodiment, the reaction time is about 1–24 h. In one embodiment, the reaction temperature is about 20–100° C. In one embodiment, the reaction is carried out using a condenser. In one embodiment, the reaction is carried out under stirring.

In one preferred embodiment, the molar ratio of the reagents mesylate (8):NaI is about 1:13; the solvent is acetone; the solvent is used in an amount of about 30 mL/mmol of mesylate; the reaction time is about 4.5 h; the reaction temperature is at reflux; under stirring.

If the mixed halo-sulfonyl product is desired, the ratio of alkaline halide:bis-sulfonyl compounds is reduced to 0.5–1:1, the reaction is stopped before completion, and the halo-sulfonyl product is isolated from the reaction mixture. An alternative method uses methanesulfonyl chloride and pyridine at an intermediate temperature; the reaction is stopped before completion and the halo-sulfonyl product is isolated from the reaction mixture. See, for example, Springer et al., 1994, Schemes 1 and 2 on page 12–13 therein, and Springer et al., 1995, compound 1c therein.

Glutamate Deprotection (GD)

In this step, one of the following three reactions is performed:

(a) a N-{4-[N,N-bis(2-sulfonyloxyethyl)amino]phenoxycarbonyl}-L-glutamate, 8, is converted to a N-{4-[N,N-bis(2-sulfonyl oxyethyl)amino]phenoxycarbonyl}-L-glutamic acid, 11:

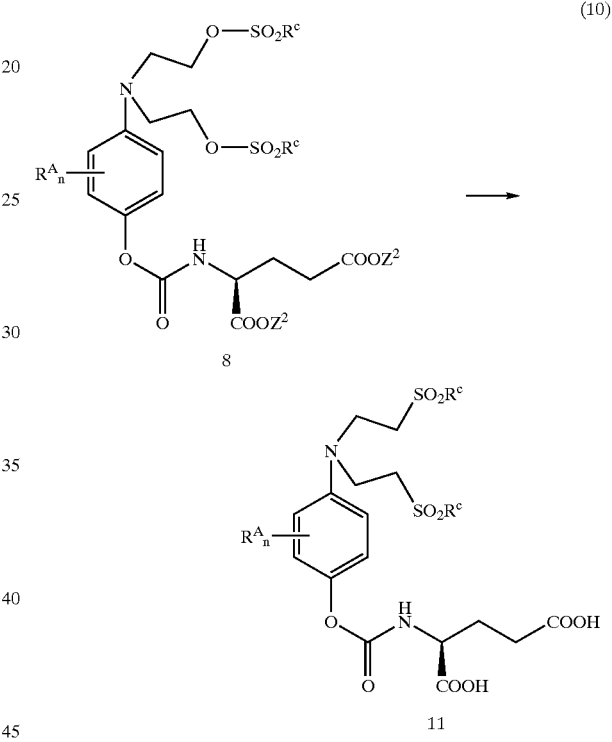

(b) an N-{4-[N,N-bis(2-haloethyl)amino]phenoxycarbonyl}-L-glutamate, 9, is converted to an N-{4-[N,N-bis(2-haloethyl)amino]phenoxycarbonyl}-L-glutamic acid, 12,

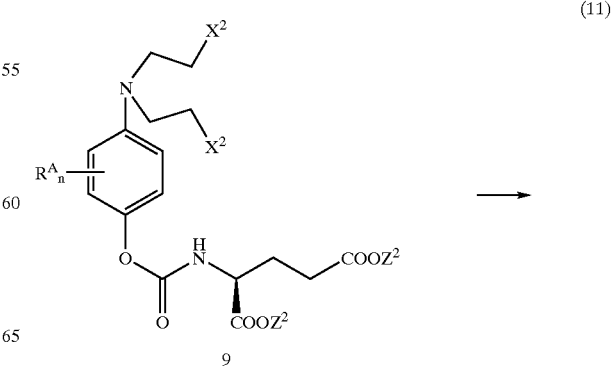

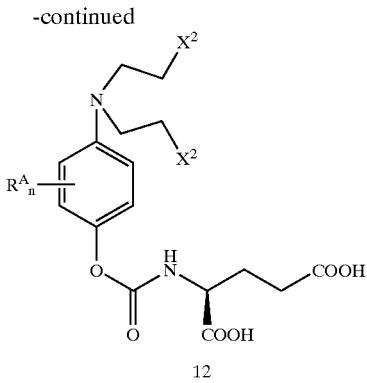

12

(c) a N-{4-[N-(2-sulfonyloxy ethyl),N-(2-haloethyl)amino]phenoxycarbonyl}-L-glutamate, 10, is converted to a deprotected mixed halo-sulfonyl product, N-{4-[N-(2-sulfonyloxyethyl),N-(2-haloethyl)amino]phenoxycarbonyl}-L-glutamic acid, 13.

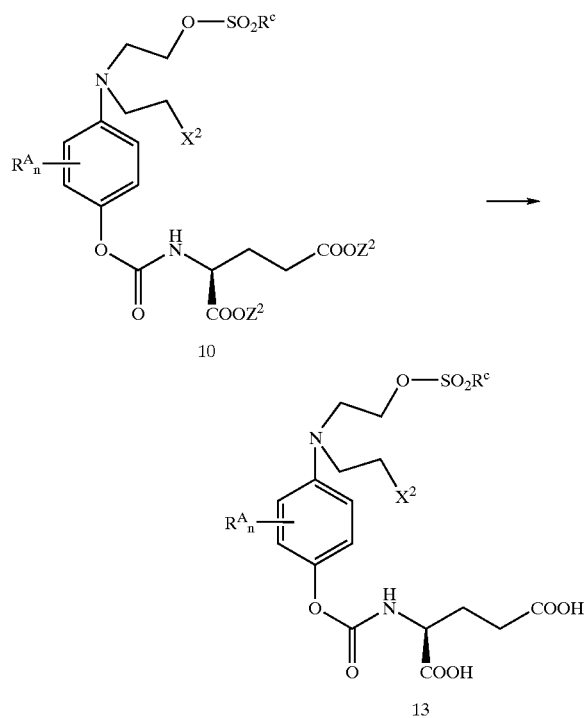

In one preferred embodiment, the reaction involves the dihalo ester, 9, and gives the dihalo acid, 12.

The glutamate ester groups, —COOZ$^2$, may be converted to acid groups, —COOH, using well know methods, and will vary according to the particular protecting group, Z$^2$. See, for example, Greene et al., 1999c.

For example, in one method, when —Z$^2$ is t-butyl, the compound may be treated with a suitable acid, for example, trifluoroacetic acid (CF$_3$COOH, TFA), optionally in a suitable solvent.

In one preferred embodiment, the solvent is trifluoroacetic acid.

In one embodiment, the molar ratio of the reagents ester (9):TFA is about 1:100–1000. In one embodiment, the solvent is used in an amount of about 5–50 mL/mmol of ester. In one embodiment, the reaction time is about 30 min to 3 h. In one embodiment, the reaction temperature is about 0–40° C. In one embodiment, the reaction is carried out under stirring.

In one preferred embodiment, the molar ratio of the reagents ester (8, 9 or 10):TFA is about 1:500; the solvent is (also) TFA; the solvent is used in an amount of about 18 mL/mmol of ester; the reaction time is about 55 min; the reaction temperature is about room temperature (e.g., about 20° C.); under stirring.

Glutamate Protection (GP)

In this (parallel) step, L-glutamic acid, 14, is converted to an L-glutamate, 15.

(13)

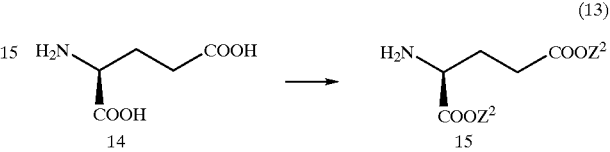

The acid groups, —COOH, of L-glutamate may be protected as esters, —COOZ$^2$, using well known methods (Greene et al, 1999c). For t-butyl esters, see for example, Ferenz et al., 1989. The group —COOZ$^2$ is a protected carboxylic acid group. The group, —Z$^2$ is a suitable carboxylic acid protecting group. In one preferred embodiment, each of the groups Z$^2$ may independently be t-butyl, allyl, or benzyl. In one preferred embodiment, each of the groups Z$^2$ is t-butyl.

For example, in one method, L-glutamic acid is reacted with isobutylene, in the presence of an acidic catalyst, for example, sulfuric acid, and optionally in a suitable solvent.

Examples of suitable solvents include aprotic organic solvents. In one preferred embodiment, the solvent is chloroform (CHCl$_3$) or dichloromethane (DCM, CH$_2$Cl$_2$). In one preferred embodiment, the solvent is chloroform.

In one embodiment, the molar ratio of the reagents glutamic acid (14):H$_2$SO$_4$:isobutylene is about 1:1.2–2:20–150. In one embodiment, the solvent is used in an amount of about 3–20 mL/mmol of glutamic acid. In one embodiment, the reaction time is about 18–120 h. In one embodiment, the reaction temperature is about −70° C. to about 25° C. In one embodiment, the reaction is carried out using an acetone-solid CO$_2$ bath, and optionally in a pressure vessel.

In one preferred embodiment, the molar ratio of the reagents glutamic acid (14):H$_2$SO$_4$:isobutylene is about 1:1.8:25; the solvent is chloroform; the solvent is used in an amount of about 4 mL/mmol of glutamic acid; the reaction time is about 18 h; the reaction temperature starts at −78° C. and is allowed to warm at room temperature.

Alternatives to the L-Glutamic Acid Moiety

The invention is described herein in detail in regard to embodiments involving an L-glumatic acid moiety:

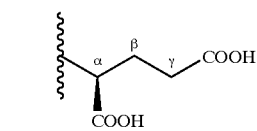

Nonetheless, in one embodiment, this group is generalised to include corresponding analogues. Examples of such analogues are described in Burke et al., 1994. Particularly preferred analogues includes those described at page 3–5 and 7 in Burke et al., 1994 (WO 94/02450).

In one embodiment, this group is generalised to include corresponding γ-analogues:

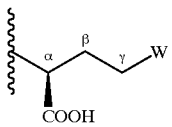

wherein W is, for example, a group denoted W as described on page 7 of Burke et al., 1994 (WO 94/02450).

In one embodiment, W is —COOH, —CONH$_2$, —CONHPh, or tetrazolyl.

In one embodiment, the glutamic acid moiety has a D-configuration, instead of an L-configuration.

In one embodiment, the L-glutamic acid moiety is generalised to include other amino acid groups, for example, aspartic acid, and amino acid oligomers, for example, Glu-Glu.

Chemical Terms

The term "carbo," "carbyl," "hydrocarbon" and "hydrocarbyl," as used herein, pertain to compounds and/or groups which have only carbon and hydrogen atoms.

The term "hetero," as used herein, pertains to compounds and/or groups which have at least one heteroatom, for example, multivalent heteroatoms (which are also suitable as ring heteroatoms) such as boron, silicon, nitrogen, phosphorus, oxygen, and sulfur, and monovalent heteroatoms, such as fluorine, chlorine, bromine, and iodine.

The term "saturated," as used herein, pertains to compounds and/or groups which do not have any carbon-carbon double bonds or carbon-carbon triple bonds.

The term "unsaturated," as used herein, pertains to compounds and/or groups which have at least one carbon-carbon double bond or carbon-carbon triple bond.

The term "aliphatic," as used herein, pertains to compounds and/or groups which are linear or branched, but not cyclic (also known as "acyclic" or "open-chain" groups).

The term "cyclic," as used herein, pertains to compounds and/or groups which have one ring, or two or more rings (e.g., spiro, fused, bridged). Compounds with one ring may be referred to as "monocyclic" or "mononuclear," whereas compounds with two or more rings may be referred to as "polycyclic" or "polynuclear."

The term "ring," as used herein, pertains to a closed ring of from 3 to 10 covalently linked atoms, more preferably 3 to 8 covalently linked atoms.

The term "aromatic ring," as used herein, pertains to a closed ring of from 3 to 10 covalently linked atoms, more preferably 5 to 8 covalently linked atoms, more preferably 5 to 6 covalently linked atoms, which ring is aromatic.

The term "heterocyclic ring," as used herein, pertains to a closed ring of from 3 to 10 covalently linked atoms, more preferably 3 to 8 covalently linked atoms, wherein at least one of the ring atoms is a multivalent ring heteroatom, for example, nitrogen, phosphorus, silicon, oxygen, and sulfur, though more commonly nitrogen, oxygen, and sulfur.

The term "alicyclic," as used herein, pertains to compounds and/or groups which have one ring, or two or more rings (e.g., spiro, fused, bridged), wherein said ring(s) are not aromatic. The term "aromatic," as used herein, pertains to compounds and/or groups which have one ring, or two or more rings (e.g., fused), wherein said ring(s) are aromatic.

The term "heterocyclic," as used herein, pertains to cyclic compounds and/or groups which have one heterocyclic ring, or two or more heterocyclic rings (e.g., spiro, fused, bridged), wherein said ring(s) may be alicyclic or aromatic.

The term "heteroaromatic," as used herein, pertains to cyclic compounds and/or groups which have one heterocyclic ring, or two or more heterocyclic rings (e.g., fused), wherein said ring(s) is aromatic.

The phrase "optionally substituted," as used herein, pertains to a parent group which may be unsubstituted or which may be substituted.

Unless otherwise specified, the term "substituted," as used herein, pertains to a parent group which bears one or more substituents. The term "substituent" is used herein in the conventional sense and refers to a chemical moiety which is covalently attached to, appended to, or if appropriate, fused to, a parent group. A wide variety of substituents are well known, and methods for their formation and introduction into a variety of parent groups are also well known.

Various substituents are described in more detail below.

$C_{1-7}$alkyl: The term "$C_{1-7}$alkyl," as used herein, pertains to a monovalent moiety obtained by removing a hydrogen atom from a $C_{1-7}$hydrocarbon compound having from 1 to 7 carbon atoms, which may be aliphatic or alicyclic, or a combination thereof, and which may be saturated, partially unsaturated, or fully unsaturated.

Examples of (unsubstituted) saturated linear $C_{1-7}$alkyl groups include, but are not limited to, methyl, ethyl, n-propyl, n-butyl, and n-pentyl (amyl).

Examples of (unsubstituted) saturated branched $C_{1-7}$alkyl groups include, but are not limited to, iso-propyl, iso-butyl, sec-butyl, tert-butyl, and neo-pentyl.

Examples of saturated alicyclic (carbocyclic) $C_{1-7}$alkyl groups (also referred to as "$C_{3-7}$cycloalkyl" groups) include, but are not limited to, unsubstituted groups such as cyclopropyl, cyclobutyl, cyclopentyl, and cyclohexyl, as well as substituted groups (e.g., groups which comprise such groups), such as methylcyclopropyl, dimethylcyclopropyl, methylcyclobutyl, dimethylcyclobutyl, methylcyclopentyl, dimethylcyclopentyl, methylcyclohexyl, dimethylcyclohexyl, cyclopropylmethyl and cyclohexylmethyl.

Examples of (unsubstituted) unsaturated $C_{1-7}$alkyl groups which have one or more carbon-carbon double bonds (also referred to as "$C_{2-7}$alkenyl" groups) include, but are not limited to, ethenyl (vinyl, —CH=CH$_2$), 2-propenyl (allyl, —CH—CH=CH$_2$), isopropenyl (—C(CH$_3$)=CH$_2$), butenyl, pentenyl, and hexenyl.

Examples of (unsubstituted) unsaturated $C_{1-7}$alkyl groups which have one or more carbon-carbon triple bonds (also referred to as "$C_{2-7}$alkynyl" groups) include, but are not limited to, ethynyl (ethinyl) and 2-propynyl (propargyl).

Examples of unsaturated alicyclic (carbocyclic) $C_{1-7}$alkyl groups which have one or more carbon-carbon double bonds (also referred to as "$C_{3-7}$cycloalkenyl" groups) include, but are not limited to, unsubstituted groups such as cyclopropenyl, cyclobutenyl, cyclopentenyl, and cyclohexenyl, as well as substituted groups (e.g., groups which comprise such groups) such as cyclopropenylmethyl and cyclohexenylmethyl.

$C_{3-20}$heterocyclyl: The term "$C_{3-20}$heterocyclyl," as used herein, pertains to a monovalent moiety obtained by removing a hydrogen atom from a ring atom of a $C_{3-20}$heterocyclic compound, said compound having one ring, or two or more rings (e.g., spiro, fused, bridged), and having from 3 to 20 ring atoms, atoms, of which from 1 to 10 are ring heteroatoms, and wherein at least one of said ring(s) is a heterocyclic ring. Preferably, each ring has from 3 to 7 ring atoms, of which from 1 to 4 are ring heteroatoms. "$C_{3-20}$" denotes ring atoms, whether carbon atoms or heteroatoms.

Examples of (non-aromatic) $C_{3-20}$heterocyclyl groups having one nitrogen ring atom include, but are not limited to, those derived from aziridine, azetidine, azetine, pyrrolidine, pyrroline, piperidine, dihydropyridine, tetrahydropyridine, and dihydropyrrole (azoline).

Examples of (non-aromatic) $C_{3-20}$heterocyclyl groups having one oxygen ring atom include, but are not limited to, those derived from oxirane, oxetane, oxolane (tetrahydrofuran), oxole (dihydrofuran), oxane (tetrahydropyran), dihydropyran, and pyran. Examples of substituted $C_{3-20}$heterocyclyl groups include sugars, in cyclic form, for example, furanoses and pyranoses, including, for example, ribose, lyxose, xylose, galactose, sucrose, fructose, and arabinose.

Examples of (non-aromatic) $C_{3-20}$heterocyclyl groups having one sulfur ring atom include, but are not limited to, those derived from thiolane (tetrahydrothiophene, thiane) and tetrahydrothiopyran.

Examples of (non-aromatic) $C_{3-20}$heterocyclyl groups having two oxygen ring atoms include, but are not limited to, those derived from dioxane.

Examples of (non-aromatic) $C_{3-20}$heterocyclyl groups having two nitrogen ring atoms include, but are not limited to, those derived from diazolidine (pyrazolidine), pyrazoline, imidazolidine, imidazoline, and piperazine.

Examples of (non-aromatic) $C_{3-20}$heterocyclyl groups having one nitrogen ring atom and one oxygen ring atom include, but are not limited to, those derived from tetrahydrooxazole, dihydrooxazole, tetrahydroisoxazole, dihydroiosoxazole, morpholine, tetrahydrooxazine, dihydrooxazine, and oxazine.

Examples of (non-aromatic) $C_{3-20}$heterocyclyl groups having one oxygen ring atom and one sulfur ring atom include, but are not limited to, those derived from oxathiolane and oxathiane.

Examples of (non-aromatic) $C_{3-20}$heterocyclyl groups having one nitrogen ring atom and one sulfur ring atom include, but are not limited to, those derived from thiazoline, thiazolidine, and thiomorpholine.

Other examples of (non-aromatic) $C_{3-20}$heterocyclyl groups include, but are not limited to, oxadiazine.

$C_{5-20}$aryl: The term "$C_{5-20}$aryl," as used herein, pertains to a monovalent moiety obtained by removing a hydrogen atom from an aromatic ring atom of a $C_{5-20}$aromatic compound, said compound having one ring, or two or more rings (e.g., fused), and having from 5 to 20 ring atoms, and wherein at least one of said ring(s) is an aromatic ring. Preferably, each ring has from 5 to 7 ring atoms.

The ring atoms may be all carbon atoms, as in "carboaryl groups," in which case the group may conveniently be referred to as a "$C_{5-20}$carboaryl" group.

Examples of $C_{5-20}$aryl groups which do not have ring heteroatoms (i.e., $C_{5-20}$carboaryl groups) include, but are not limited to, those derived from benzene (i.e., phenyl) ($C_6$), naphthalene ($C_{10}$), anthracene ($C_{14}$), phenanthrene ($C_{14}$), pyrene ($C_{16}$), and naphthacene ($C_{18}$).

Alternatively, the ring atoms may include one or more heteroatoms, including but not limited to oxygen, nitrogen, and sulfur, as in "heteroaryl groups." In this case, the group may conveniently be referred to as a "$C_{5-20}$heteroaryl" group, wherein "$C_{5-20}$" denotes ring atoms, whether carbon atoms or heteroatoms. Preferably, each ring has from 5 to 7 ring atoms, of which from 0 to 4 are ring heteroatoms.

Examples of $C_{5-20}$heteroaryl groups include, but are not limited to, $C_5$heteroaryl groups derived from furan (oxole), thiophene (thiole), pyrrole (azole), imidazole (1,3-diazole), pyrazole (1,2-diazole), triazole, oxazole, isoxazole, thiazole, isothiazole, oxadiazole, and oxatriazole; and $C_6$heteroaryl groups derived from isoxazine, pyridine (azine), pyridazine (1,2-diazine), pyrimidine (1,3-diazine; e.g., cytosine, thymine, uracil), pyrazine (1,4-diazine), triazine, tetrazole, and tetradiazole (furazan).

Examples of $C_{5-20}$heterocyclic groups (including $C_{5-20}$heteroaryl groups) which comprise fused rings, include, but are not limited to, $C_9$heterocyclic groups derived from benzofuran, isobenzofuran, indole, isoindole, purine (e.g., adenine, guanine), benzimidazole; $C_{10}$heterocyclic groups derived from quinoline, isoquinoline, benzodiazine, pyridopyridine, quinoxaline; $C_{13}$heterocyclic groups derived from carbazole; $C_{14}$heterocyclic groups derived from acridine, xanthene, phenoxathiin, phenazine, phenoxazine, phenothiazine.

The above $C_{1-7}$alkyl, $C_{3-20}$heterocyclyl, and $C_{5-20}$aryl groups, whether alone or part of another substituent, may themselves optionally be substituted with one or more groups selected from themselves and the additional substituents listed below.

Hydrogen: —H. Note that if the substituent at a particular position is hydrogen, it may be convenient to refer to the compound as being "unsubstituted" at that position.

Halo: —F, —Cl, —Br, and —I.

Hydroxy: —OH.

Ether: —OR, wherein R is an ether substituent, for example, a $C_{1-7}$alkyl group (also referred to as a $C_{1-7}$alkoxy group, discussed below), a $C_{3-20}$heterocyclyl group (also referred to as a $C_{3-20}$heterocyclyloxy group), or a $C_{5-20}$aryl group (also referred to as a $C_{5-20}$aryloxy group), preferably a $C_{1-7}$alkyl group.

$C_{1-7}$alkoxy: —OR, wherein R is a $C_{1-7}$alkyl group. Examples of $C_{1-7}$alkoxy groups include, but are not limited to, —OCH$_3$ (methoxy), —OCH$_2$CH$_3$ (ethoxy) and —OC(CH$_3$)$_3$ (tert-butoxy).

Formyl (carbaldehyde, carboxaldehyde): —C(=O)H.

Acyl (keto): —C(=O)R, wherein R is an acyl substituent, for example, a $C_{1-7}$alkyl group (also referred to as $C_{1-7}$alkylacyl or $C_{1-7}$alkanoyl), a $C_{3-20}$heterocyclyl group (also referred to as $C_{3-20}$heterocyclylacyl), or a $C_{5-20}$aryl group (also referred to as $C_{5-20}$arylacyl), preferably a $C_{1-7}$alkyl group. Examples of acyl groups include, but are not limited to, —C(=O)CH$_3$ (acetyl), —C(=O)CH$_2$CH$_3$ (propionyl), —C(=O)C(CH$_3$)$_3$ (butyryl), and —C(=O)Ph (benzoyl, phenone).

Acylhalide (haloformyl, halocarbonyl): —C(=O)X, wherein X is —F, —Cl, —Br, or —I, preferably —Cl, —Br, or —I.

Carboxy (carboxylic acid): —COOH.

Ester (carboxylate, carboxylic acid ester, oxycarbonyl): —C(=O)OR, wherein R is an ester substituent, for example, a $C_{1-7}$alkyl group, a $C_{3-20}$heterocyclyl group, or a $C_{5-20}$aryl group, preferably a $C_{1-7}$alkyl group. Examples of ester groups include, but are not limited to, —C(=O)OCH$_3$, —C(=O)OCH$_2$CH$_3$, —C(=O)OC(CH$_3$)$_3$, and —C(=O)OPh.

Acyloxy (reverse ester): —OC(=O)R, wherein R is an acyloxy substituent, for example, a $C_{1-7}$alkyl group, a $C_{3-20}$heterocyclyl group, or a $C_{5-20}$aryl group, preferably a $C_{1-7}$alkyl group. Examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, and —OC(=O)CH$_2$Ph.

Amido (carbamoyl, carbamyl, aminocarbonyl, carboxamide): —C(=O)NR$^1$R$^2$, wherein R$^1$ and R$^2$ are independently amino substituents, as defined for amino groups. Examples of amido groups include, but are not limited to, —C(=O)NH$_2$, —C(=O)NHCH$_3$, —C(=O)NH(CH$_3$)$_2$, —C(=O)NHCH$_2$CH$_3$, and —C(=O)N(CH$_2$CH$_3$)$_2$, as well as amido groups in which R$^1$ and R$^2$, together with the nitrogen atom to which they are attached, form a heterocyclic structure as in, for example, piperidinocarbonyl, morpholinocarbonyl, thiomorpholinocarbonyl, and piperazinocarbonyl.

Acylamido (acylamino): —NR$^1$C(=O)R$^2$, wherein R$^1$ is an amide substituent, for example, a $C_{1-7}$alkyl group, a $C_{3-20}$heterocyclyl group, or a $C_{5-20}$aryl group, preferably a $C_{1-7}$alkyl group, and R$^2$ is an acyl substituent, for example, a $C_{1-7}$alkyl group, a $C_{3-20}$heterocyclyl group, or a $C_{5-20}$aryl group, preferably a $C_{1-7}$alkyl group. Examples of acylamide groups include, but are not limited to, —NHC(=O)CH$_3$, —NHC(=O)CH$_2$CH$_3$, and —NHC(=O)Ph. R$^1$ and R$^2$ may together form a cyclic structure, as in, for example, succinimidyl and maleimidyl:

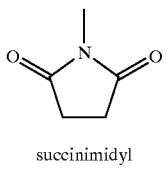  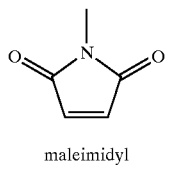

succinimidyl    maleimidyl

Thioamido (thiocarbamyl): —C(=S)NR$^1$R$^2$, wherein R$^1$ and R$^2$ are independently amino substituents, as defined for amino groups. Examples of amido groups include, but are not limited to, —C(=S)NH$_2$, —C(=S)NHCH$_3$, —C(=S)NH(CH$_3$)$_2$, and —C(=S)NHCH$_2$CH$_3$.

Tetrazolyl: a five membered aromatic ring having four nitrogen atoms and one carbon atom,

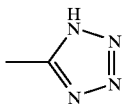

Amino: —NR$^1$R$^2$, wherein R$^1$ and R$^2$ are independently amino substituents, for example, hydrogen, a $C_{1-7}$alkyl group (also referred to as $C_{1-7}$alkylamino or di-$C_{1-7}$alkylamino), a $C_{3-20}$heterocyclyl group, or a $C_{5-20}$aryl group, preferably H or a $C_{1-7}$alkyl group, or, in the case of a "cyclic" amino group, R$^1$ and R$^2$, taken together with the nitrogen atom to which they are attached, form a heterocyclic ring having from 4 to 8 ring atoms. Examples of amino groups include, but are not limited to, —NH$_2$, —NHCH$_3$, —NHCH(CH$_3$)$_2$, —N(CH$_3$)$_2$, —N(CH$_2$CH$_3$)$_2$, and —NHPh. Examples of cyclic amino groups include, but are not limited to, aziridino, azetidino, piperidino, piperazino, morpholino, and thiomorpholino.

Nitro: —NO$_2$.
Nitroso: —NO.
Azido: —N$_3$.
Cyano (nitrile, carbonitrile): —CN.
Isocyano: —NC.
Cyanato: —OCN.
Isocyanato: —NCO.
Thiocyano (thiocyanato): —SCN.
Isothiocyano (isothiocyanato): —NCS.
Sulfhydryl (thiol, mercapto): —SH.
Thioether (sulfide): —SR, wherein R is a thioether substituent, for example, a $C_{1-7}$alkyl group (also referred to as a $C_{1-7}$alkylthio group), a $C_{3-20}$heterocyclyl group (also referred to as a $C_{3-20}$heterocyclylthio group), or a $C_{5-20}$aryl group (also referred to as a $C_{5-20}$arylthio group), preferably a $C_{1-7}$alkyl group. Examples of $C_{1-7}$alkylthio groups include, but are not limited to, —SCH$_3$ and —SCH$_2$CH$_3$.

Sulfonic acid (sulfo): —S(=O)$_2$OH.
Sulfonate (sulfonic acid ester): —S(=O)$_2$OR, wherein R is a sulfonate substituent, for example, a $C_{1-7}$alkyl group, a $C_{3-20}$heterocyclyl group, or a $C_{5-20}$aryl group, preferably a $C_{1-7}$alkyl group. Examples of sulfonate groups include, but are not limited to, —S(=O)$_2$OCH$_3$ and —S(=O)$_2$OCH$_2$CH$_3$.
Sulfone (sulfonyl): —S(=O)$_2$R, wherein R is a sulfone substituent, for example, a $C_{1-7}$alkyl group, a $C_{3-20}$heterocyclyl group, or a $C_{5-20}$aryl group, preferably a $C_{1-7}$alkyl group. Examples of sulfone groups include, but are not limited to, —S(=O)$_2$CH$_3$ (methanesulfonyl, mesyl), —S(=O)$_2$CF$_3$, —S(=O)$_2$CH$_2$CH$_3$, and 4-methylphenylsulfonykl(tosyl).
Sulfonyloxy: —OS(=O)$_2$R, wherein R is a sulfonyloxy substituent, for example, a $C_{1-7}$alkyl group, a $C_{3-20}$heterocyclyl group, or a $C_{5-20}$aryl group, preferably a $C_{1-7}$alkyl group. Examples of sulfonyloxy groups include, but are not limited to, —OS(=O)$_2$CH$_3$ and —OS(=O)$_2$CH$_2$CH$_3$.
Sulfinyloxy: —OS(=O)R, wherein R is a sulfinyloxy substituent, for example, a $C_{1-7}$alkyl group, a $C_{3-20}$heterocyclyl group, or a $C_{5-20}$aryl group, preferably a $C_{1-7}$alkyl group. Examples of sulfinyloxy groups include, but are not limited to, —OS(=O)CH$_3$ and —OS(=O)CH$_2$CH$_3$.
Sulfamino: —NR$^1$S(=O)$_2$OH, wherein R$^1$ is an amino substituent, as defined for amino groups. Examples of sulfamino groups include, but are not limited to, —NHS(=O)$_2$OH and —N(CH$_3$)S(=O)$_2$OH.
Sulfonamino: —NR$^1$S(=O)$_2$R, wherein R$^1$ is an amino substituent, as defined for amino groups, and R is a sulfonamino substituent, for example, a $C_{1-7}$alkyl group, a $C_{3-20}$heterocyclyl group, or a $C_{5-20}$aryl group, preferably a $C_{1-7}$alkyl group.
Examples of sulfonamino groups include, but are not limited to, —NHS(=O)$_2$CH$_3$ and —N(CH$_3$)S(=O)$_2$C$_6$H$_5$.
Sulfinamino: —NR$^1$S(=O)R, wherein R$^1$ is an amino substituent, as defined for amino groups, and R is a sulfinamino substituent, for example, a $C_{1-7}$alkyl group, a $C_{3-20}$heterocyclyl group, or a $C_{5-20}$aryl group, preferably a $C_{1-7}$alkyl group. Examples of sulfinamino groups include, but are not limited to, —NHS(=O)CH$_3$ and —N(CH$_3$)S(=O)C$_6$H$_5$.
Sulfamyl: —S(=O)NR$^1$R$^2$, wherein R$^1$ and R$^2$ are independently amino substituents, as defined for amino groups. Examples of sulfamyl groups include, but are not limited to, —S(=O)NH$_2$, —S(=O)NH(CH$_3$), —S(=O)N(CH$_3$)$_2$, —S(=O)NH(CH$_2$CH$_3$), —S(=O)N(CH$_2$CH$_3$)$_2$, and —S(=O)NHPh.
Sulfonamido: —S(=O)$_2$NR$^1$R$^2$, wherein R$^1$ and R$^2$ are independently amino substituents, as defined for amino groups. Examples of sulfonamido groups include, but are not limited to, —S(=O)$_2$NH$_2$, —S(=O)$_2$NH(CH$_3$), —S(=O)$_2$N(CH$_3$)$_2$, —S(=O)$_2$NH(CH$_2$CH$_3$), —S(=O)$_2$N(CH$_2$CH$_3$)$_2$, and —S(=O)$_2$NHPh.

For example, a $C_{1-7}$alkyl group may be substituted with, for example, hydroxy (also referred to as a $C_{1-7}$hydroxyalkyl group), $C_{1-7}$alkoxy (also referred to as a $C_{1-7}$alkoxyalkyl group), amino (also referred to as a $C_{1-7}$aminoalkyl group), halo (also referred to as a $C_{1-7}$haloalkyl group), carboxy (also referred to as a $C_{1-7}$carboxyalkyl group), and $C_{5-20}$aryl (also referred to as a $C_{5-20}$aryl-$C_{1-7}$alkyl group).

Similarly, a $C_{5-20}$aryl group may be substituted with, for example, hydroxy (also referred to as a $C_{5-20}$hydroxyaryl group), halo (also referred to as a $C_{5-20}$haloaryl group), amino (also referred to as a $C_{5-20}$aminoaryl group, e.g., as in aniline), $C_{1-7}$alkyl (also referred to as a $C_{1-7}$alkyl-$C_{5-20}$aryl group, e.g., as in toluene), and $C_{1-7}$alkoxy (also referred to as a $C_{1-7}$alkoxy-$C_{5-20}$aryl group, e.g., as in anisole).

These and other specific examples of such substituted groups are also discussed below.

$C_{1-7}$haloalkyl group: The term "$C_{1-7}$haloalkyl group," as used herein, pertains to a $C_{1-7}$alkyl group in which at least one hydrogen atom (e.g., 1, 2, 3) has been replaced with a halogen atom (e.g., F, Cl, Br, I). If more than one hydrogen atom has been replaced with a halogen atom, the halogen atoms may independently be the same or different. Every hydrogen atom may be replaced with a halogen atom, in which case the group may conveniently be referred to as a "$C_{1-7}$perhaloalkyl group." Examples of $C_{1-7}$haloalkyl groups include, but are not limited to, —$CF_3$, —$CHF_2$, —$CH_2F$, —$CCl_3$, —$CBr_3$, —$CH_2CH_2F$, —$CH_2CHF_2$, and —$CH_2CF_3$.

$C_{1-7}$haloalkoxy: —OR, wherein R is a $C_{1-7}$haloalkyl group. Examples of $C_{1-7}$haloalkoxy groups include, but are not limited to, —$OCF_3$, —$OCHF_2$, —$OCH_2F$, —$OCCl_3$, —$OCBr_3$, —$OCH_2CH_2F$, —$OCH_2CHF_2$, and —$OCH_2CF_3$.

$C_{1-7}$hydroxyalkyl: The term "$C_{1-7}$hydroxyalkyl group," as used herein, pertains to a $C_{1-7}$alkyl group in which at least one hydrogen atom has been replaced with a hydroxy group. Examples of $C_{1-7}$hydroxyalkyl groups include, but are not limited to, —$CH_2OH$, —$CH_2CH_2OH$, and —CH(OH)$CH_2OH$.

$C_{1-7}$carboxyalkyl: The term "$C_{1-7}$carboxyalkyl group," as used herein, pertains to a $C_{1-7}$alkyl group in which at least one hydrogen atom has been replaced with a carboxy group. Examples of $C_{1-7}$carboxyalkyl groups include, but are not limited to, —$CH_2COOH$ and —$CH_2CH_2COOH$.

$C_{1-7}$aminoalkyl: The term "$C_{1-7}$aminoalkyl group," as used herein, pertains to a $C_{1-7}$alkyl group in which at least one hydrogen atom has been replaced with an amino group. Examples of $C_{1-7}$aminoalkyl groups include, but are not limited to, —$CH_2NH_2$, —$CH_2CH_2NH_2$, and —$CH_2CH_2N(CH_3)_2$.

$C_{1-7}$alkyl-$C_{5-20}$aryl: The term "$C_{1-7}$alkyl-$C_{5-20}$aryl," as used herein, describes certain $C_{5-20}$aryl groups which have been substituted with a $C_{1-7}$alkyl group. Examples of such groups include, but are not limited to, tolyl (as in toluene), xylyl (as in xylene), mesityl (as in mesitylene), styryl (as in styrene), and cumenyl (as in cumene).

$C_{1-7}$alkyl-$C_{5-20}$aryloxy: The term "$C_{1-7}$alkyl-$C_{5-20}$aryloxy," as used herein, describes certain $C_{5-20}$aryloxy groups which have been substituted with a $C_{1-7}$alkyl group. Examples of such groups include, but are not limited to, tolyloxy, xylyloxy, mesityloxy, and cumenyloxy.

$C_{5-20}$aryl-$C_{1-7}$alkyl: The term "$C_{5-20}$aryl-$C_{1-7}$alkyl," as used herein, describers certain $C_{1-7}$alkyl groups which have been substituted with a $C_{5-20}$aryl group. Examples of such groups include, but are not limited to, benzyl (phenylmethyl), tolylmethyl, phenylethyl, and triphenylmethyl (trityl).

$C_{5-20}$aryl-$C_{1-7}$alkoxy: The term "$C_{5-20}$aryl-$C_{1-7}$alkoxy," as used herein, describes certain $C_{1-7}$alkoxy groups which have been substituted with a $C_{5-20}$aryl group. Examples of such groups include, but are not limited to, benzyloxy, tolylmethoxy, and phenylethoxy.

$C_{5-20}$haloaryl: The term "$C_{5-20}$haloaryl," as used herein, describes certain $C_{5-20}$aryl groups which have been substituted with one or more halo groups. Examples of such groups include, but are not limited to, halophenyl (e.g., fluorophenyl, chlorophenyl, bromophenyl, or iodophenyl, whether ortho-, meta-, or para-substituted), dihalophenyl, trihalophenyl, tetrahalophenyl, and pentahalophenyl.

Isomers, Salts, Solvates, and Protected Forms

Certain compounds may exist in one or more particular geometric, optical, enantiomeric, diastereomeric, epimeric, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers," as used herein, are structural (or constitutional) isomers (i.e., isomers which differ in the connections between atoms rather than merely by the position of atoms in space). For example, a reference to a methoxy group, —$OCH_3$, is not to be construed as a reference to its structural isomer, a hydroxymethyl group, —$CH_2OH$. Similarly, a reference to ortho-chlorophenyl is not to be construed as a reference to its structural isomer, meta-chlorophenyl. However, a reference to a class of structures may well include structurally isomeric forms falling within that class (e.g., $C_{1-7}$alkyl includes n-propyl and isopropyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hyroxyazo, and nitro/aci-nitro.

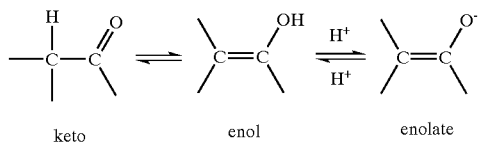

keto      enol      enolate

Note that specifically included in the term "isomer" are compounds with one or more isotopic substitutions. For example, H may be in any isotopic form, including $^1H$, $^2H$ (D), and $^3H$ (T); C may be in any isotopic form, including $^{12}C$, $^{13}C$, and $^{14}C$; O may be in any isotopic form, including $^{16}O$ and $^{18}O$; and the like.

Unless otherwise specified, a reference to a particular compound includes all such isomeric forms, including (wholly or partially) racemic and other mixtures thereof. Methods for the preparation (e.g., asymmetric synthesis) and separation (e.g., fractional crystallisation and chromatographic means) of such isomeric forms are either known in the art or are readily obtained by adapting the methods taught herein, or known methods, in a known manner.

Unless otherwise specified, a reference to a particular compound also includes ionic, salt, solvate, and protected forms of thereof.

Solvents

Solvents may conveniently be classified according to one or more of their physical or chemical properties.

For example, solvents may be classified according to their polarity, that is, their permanent dipole moment. Examples of highly polar solvents include dimethylformamide (DMF), dimethylacetamide, and acetonitrile (ACN). Examples of moderately polar solvents include acetone, methanol, tetrahydrofuran (THF), ethyl acetate (AcOEt), and water. Examples of relatively non-polar solvents include diethyl ether, chloroform, and dichloromethane (DCM). Examples of non-polar and virtually non-polar solvents include alkanes, benzene, toluene, and carbon tetrachloride.

Solvents may also be classified as "protic" or "aprotic" according to their proton-exchange properties. Protic solvents accept and/or donate protons. Examples of protic solvents include water, alcohols, carboxylic acids (e.g., acetic acid), and amines (e.g., ammonia, pyridine). Aprotic solvents neither accept nor donate protons. Examples of aprotic solvents include carbon tetrachloride, chloroform, dichloromethane (DCM), acetonitrile (ACN), ethyl acetate (AcOEt), dimethylacetamide, tetrahydrofuran (THF), dimethylformamide (DMF), toluene, benzene, acetone, ethers (e.g., diethyl ether), alkanes (e.g., hexane), dimethylsulfoxide (DMSO), sulfur dioxide, hexamethylphosphoramide (HMPA), and, tetramethylurea. Amphoteric solvents, such as water, are capable of both accepting and donating protons.

Solvents may also be classified as "organic" or "inorganic" according to their chemical composition. Conventionally, organic solvents comprise, at least, carbon atoms, while inorganic solvents do not. Examples of inorganic solvents include water, ammonia, and sulfur dioxide.

Advantages of the Present Invention

Advantageously, the methods of the present invention permit an improved overall yield of prodrug, 11, 12 or 13, calculated with respect to glutamic acid, 14, which is much greater than that obtained using previously published methods (see, for example, Heaton, D. W., et al., 1996). The present method gives a yield, for 12A, of 55.4% with respect to glutamic acid, 14, whereas the previously published method gives a yield of only 13.2%.

Hydroxyethylation of benzyloxyaniline, 1A, with ethylene oxide, gives the diol, 2A, in 84% yield. Protection of the diol, 2A, with silyl chloride and imidazole in DMF, gives the benzyl ether silyloxy compound, 3A, in 95% yield, after purification. Deprotection of the benzyl ether silyloxy compound, 3A, by catalytic hydrogenation, gives the silyloxy phenol, 4A, in 100% yield. Thus, the silyloxy phenol, 4A, is obtained in (84%)(95%)(100%) or 79.8% yield with respect to the benzyloxyaniline, 1A.

Di-t-butyl glutamate, 15A, was prepared by reaction of glutamic acid, 14, with isobutylene in the presence of sulfuric acid, in 83% yield, a better yield than that reported in the literature (see, for example, Ferenz, C. R., et al., 1989).

4-[N,N-bis(2-(t-butyldimethylsilyloxy)ethyl)amino]-phenol, 4A, is converted to chloroformate, 5A, and chloroformate, 5A, is coupled with di-t-butyl glutamate, 15A, to afford 6A, in a total yield of 90% with respect to glutamate, 15A.

The bis-silyl ether, 6A, is cleanly deprotected with NEt$_3$.3HF to give the key intermediate, 7A, in 97% yield. After a simple work up (extraction with water and Na$_2$CO$_3$), 7A is obtained without need of further purification.

Mesylation of the bishydroxy compound, 7A, with mesyl anhydride in dichloromethane, gives the bis-mesyl compound, 8A. After aqueous extraction with citric acid, the bis-mesyl compound, 8A, is converted to the bis-iodo compound, 9A, by treatment with NaI in refluxing acetone, in 85% yield after purification, with respect to 7A.

Final deprotection of the bis-iodo compound, 9A, with TFA and recrystallisation from toluene:ethyl acetate, yielded the prodrug, 12A, in 90% yield.

The overall yield of prodrug, 12A, with respect to glutamic acid, 14, is (83%)(90%)(97%)(85%)(90%) or 55.4%, more than three times higher then the 13.2% yield of the previously published method (see for example, Heaton, D. W., et al., 1996).

Also advantageously, in the methods of the present invention, the synthesis of the key intermediate, 7A, is much improved, avoiding the low yield steps of: (a) 4-nitrophenyl chloroformate coupling (77% with respect to glutamic acid), (b) reduction of nitroderivative to amine (58%); and, (c) hydroxyethylation, which is generally a difficult and low yield reaction (49%).

Also advantageously, in the methods of the present invention, the coupling of 5A with 15A is reliable and proceeds with higher yield than the coupling of 4-nitrophenyl chloroformate with glutamic acid, which often produces ureas as by-products.

Also advantageously, in the methods of the present invention, (a) hydroxyethylation is performed on 4-benzyloxyaniline, 1A, instead of the more expensive and advanced intermediate di-t-butyl, N-(4-aminophenoxycarbonyl)-L-glutamate, (b) this step proceeds with yields up to 84% and (c) the work-up is simplified.

Also advantageously, in the methods of the present invention, the glutamate is introduced at a later step, and so the overall process is more economic in this expensive starting material.

EXAMPLES

The following are examples are provided solely to illustrate the present invention and are not intended to limit the scope of the invention, as described herein.

Example 1

4-Benzyloxy-N,N-bis(2-hydroxyethyl)aniline (2A)

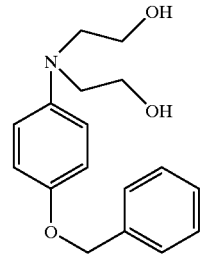

4-Benzyloxyaniline hydrochloride 1A (9.32 g, 39.5 mmol) was dissolved in acetic acid (400 mL), triethylamine (6 mL, 43 mmol) was added followed by ethylene oxide (20 mL). The reaction mixture was stirred at room temperature for 72 h, the solvent was evaporated in a rotary evaporator under water pump then under oil pump at 50° C. for 1 h. The residue was then diluted with water (500 mL) and the precipitate recovered by filtration, washed with more water, then dried in dessicator over P$_2$O$_5$ to afford 2A (9.6 g, 84%) as a pale brown powder.

$^1$H-NMR (DMSO-d$_6$) $\delta_H$: 3.32 (t, 4H, N(CH$_2$CH$_2$OH)$_2$), 3.42–3.52 (m, 4H, N(CH$_2$CH$_2$OH)$_2$), 4.65 (t, 2H, OH, J=5.90 Hz), 4.97 (s, 2H, PhCH$_2$), 6.60 (d, 2H,) H$_{arom3+5}$, J=9.10 Hz), 6.83 (d, 2H, H$_{arom2+6}$), 7.25–7.44 (m, 5H, H$_{arombenzyl}$)

Example 2

4-Benzyloxy-N,N-bis[2-(t-butyldimethylsilyloxy)ethyl]aniline (3A)

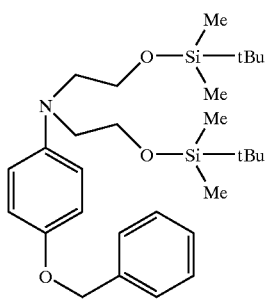

A mixture of 2A (9.6 g, 33.4 mmol), t-butyldimethylsilyl chloride (12.7 g, 84 mmol) and imidazole (7.8 g, 130 mmol) were dissolved in dry DMF (80 mL) and the reaction stirred overnight, then the solvent was evaporated, the residue taken in dichloromethane, the precipitated imidazole hydrochloride filtered off, and the filtrate evaporated. The residue was purified by column chromatography on silica (cyclohexane:ethyl acetate 4:1), to afford 3A (16.4 g, 95%) as an oil.

$^1$H-NMR (DMSO-$d_6$) $\delta_H$: −0.01 (s, 12H, 2×SiMe$_2$), 0.84 (s, 18H, 2×Sit-Bu), 3.39 (t, 4H, N(CH$_2$CH$_2$OSi)$_2$, J=5.98 Hz), 3.67 (t, 4H, N(CH$_2$CH$_2$OSi)$_2$), 4.96 (s, 2H, PhCH$_2$), 6.59 (d, 2H, H$_{arom3+5}$, J=9.03 Hz), 6.82 (d, 2H, H$_{arom2+6}$), 7.25–7.44 (m, 5H, H$_{arom\ benzyl}$).

Example 3

4-{N,N-bis[2-(t-butyldimethylsilyloxy)ethyl]amino}-phenol (4A)

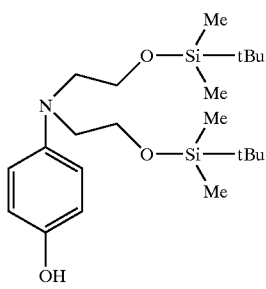

The benzyl ether 3A (11.4 g, 22.1 mmol) was dissolved in THF, Pd/C catalyst (1.6 g) was added and the suspension stirred overnight under H$_2$ atmosphere. The catalyst was filtered off, the solvent evaporated to afford 4A (9.4 g, 100%) as an oil.

$^1$H-NMR (DMSO-$d_6$) $\delta_H$: 0.00 (s, 12H, SiMe$_2$), 0.84 (s, 18H, Sit-Bu), 3.34 (t, 4H, N(CH$_2$CH$_2$OSi)$_2$, J=6.07 Hz), 3.65 (t, 4H, N(CH$_2$CH$_2$OSi)$_2$), 6.51 (d, 2H, H$_{arom2+6}$, J=9.23 Hz), 6.58 (d, 2H, H$_{arom3+5}$), 8.46 (s, 1H, OH).

Example 4

4-[N,N-bis(2-silyloxyethyl)amino]phenyl chloroformate (5A)

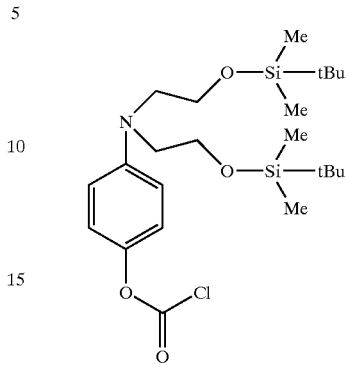

In a stirred solution of 4A (13.2 g, 32 mmol) in toluene (120 mL), phosgene 20% solution in toluene (35 mL, 70 mmol) was added at once at room temperature. After 2 min, triethylamine (5.3 mL, 38 mmol) was added dropwise, and the formation of chloroformate 5A was complete in 10 min as detected by IR spectra ($V_{OCOCl}$=1784 cm$^{-1}$). The solution was filtered and the filtrate evaporated to afford an oil, which was dissolved in THF (80 mL) and used in the glutamate conjugation reaction.

Example 5

Di-t-butyl L-glutamate Hydrochloride (15A)

Glutamic acid 14 (4.4 g, 30 mmol) was suspended in chloroform (120 mL) and sulfuric acid (3 mL, 56 mmol) was added. The suspension was cooled at −78° C. and condensed isobutylene (70 mL) was added. The reaction mixture was stirred allowing to warm to room temperature for 18 h. After 18 hr, all the suspended solid had dissolved to a clear solution. Nitrogen was bubbled through the solution for 10 min, then it was extracted with aqueous NaHCO$_3$ (2×100 mL) and distilled water (100 mL). The organic layer was dried (MgSO$_4$), evaporated, and kept in a dessicator over NaOH pellets for 48 h to afford 15 (6.7 g, 86%) as an oil.

$^1$H-NMR $\delta_H$: 1.39 (s, 9H, COO-t-Bu), 1.41 (s, 9H, COO-t-Bu), 1.60–1.90 (2 m, 2H, CH$_2$CH(NH$_2$)—), 2.15–2.35 (m, 2H, CH$_2$COO), 2.85 (s, 2H, NH$_2$), 3.20–3.35 m, 1H, CH(NH$_2$)—). MS (ESI): 260 (M$^+$+H, 100), 283 (M$^+$+Na, 10).

Glutamate, 15 (604 mg, 2.33 mmol) was dissolved in dry diethyl ether (50 mL) and 1 M HCl in diethyl ether (2.33 mL, 1 eq.) was added. The solution was stirred for 5 min, then the solvent was diluted with hexane, and then evaporated. The residue dissolved partially in hexane without crystallisation; therefore it was redissolved in diethyl ether, and 1 M HCl in diethyl ether (2 mL, 0.86 eq.) was added. The solution was stirred for 10 min, then the solvent was diluted with hexane and heated at reflux for 5 min. The solution was cooled on ice bath at room temperature, then was evaporated to afford an oily residue. The residue was scratched with hexane and was left for 18 h in hexane to crystallise. The crystals were washed with hexane, to afford 15.HCl (15A) as a white solid (624 mg). The hexane washing afforded a second crop of crystals of 15.HCl (15A) (38 mg). The total yield of 15.HCl (15A) was 662 mg (96%) and the yield of esterification, hydrochloride formation, and crystallisation is (86%) (96%)=83%.

$^1$H-NMR $\delta_H$: 1.40 (s, 9H, COO-t-Bu), 1.45 (s, 9H, COO-t-Bu), 1.90–2.01 (q, 2H, CH$_2$CH(NH$_2$)—), 2.20–2.50 (m, 2H, CH$_2$COO), 3.87 (t, 1H, CH(NH$_2$)—, J=6.62 Hz), 8.40 (s, 3H, NH$_3^+$).

Example 6

Di-t-butyl, N-{4-[N,N-bis(2-(t-butyldimethylsilyloxy)ethyl)amino]-phenoxycarbonyl}-L-glutamate (6A)

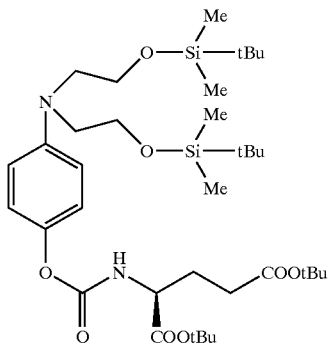

Di-t-butyl L-glutamate hydrochloride 15A (9.77 g, 33 mmol) was dissolved in ethyl acetate (100 mL) and extracted with aq. Na$_2$CO$_3$ (100 mL). The organic layer was dried (MgSO$_4$) and evaporated. The oily residue was dissolved in THF (80 mL). The solution of chloroformate 5A (obtained from 13.2 g 4A as described in Example 4) in THF was poured over the solution of di-t-butyl glutamate 15A under stirring, at room temperature, followed by triethylamine (4.9 mL, 35 mmol). After 5 min the reaction was completed, as monitored by IR (the peak of chloroformate V$_{OCOCl}$=1784 cm$^{-1}$ disappeared). The precipitate was filtered off, the solvent evaporated and the residue purified by column chromatography on silica (cyclohexane:ethyl acetate 4:1) to afford 6A (20.45 g, 90%) as an oil.

$^1$H-NMR (DMSO-d$_6$) $\delta_H$: 0.00 (s, 12H, 2×SiMe$_2$), 0.84 (s, 18H, 2×Sit-Bu), 1.39 (s, 9H, COO-t-Bu), 1.40 (s, 9H, COO-t-Bu), 1.75–2.05 (2m, 2H, CH$_2$CH(NH)—), 2.32 (t, 2H, CH$_2$COO, J=7.69 Hz), 3.44 (t, 4H, N(CH$_2$CH$_2$OSi)$_2$, J=5.83 Hz), 3.70 (t, 4H, N(CH$_2$CH$_2$OSi)$_2$), 3.90–4.05 (m, 1H, CH(NH)—), 6.61 (d, 2H, H$_{arom2+6}$, J=9.10 Hz), 6.83 (d, 2H, H$_{arom3+5}$), 7.87 (d, 1H, NH-G, J=7.85 Hz).

Example 7

Di-t-butyl, N-{4-[N,N-bis(2-hydroxyethyl)amino]-phenoxycarbonyl}-L-glutamate (7A)

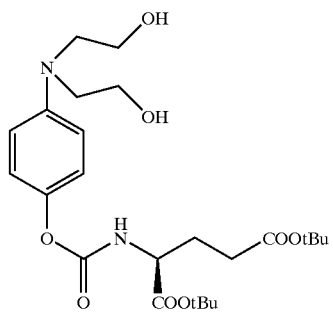

NEt$_3$.3HF (42 mL) was added to a solution of 6A (20.45 g, 28.8 mmol) in THF (315 mL). The solution was stirred at room temperature for 12 h, then the solvent was evaporated, the residue was taken in ethyl acetate (100 mL) and extracted with water (100 mL), aq. Na$_2$CO$_3$ (100 mL) and water again (100 mL). The organic layer was dried (MgSO$_4$) and evaporated to afford 7A (13.4 g, 97%) as a foamy solid.

$^1$H-NMR (DMSO-d$_6$) $\delta_H$: 1.39 (s, 9H, COO-t-Bu), 1.40 (s, 9H, COO-t-Bu), 1.70–2.00 (2m, 2H, CH$_2$CH(NH)—), 2.32 (t, 2H, CH$_2$COO, J=7.63 Hz), 3.37 (t, 4H, N(CH$_2$CH$_2$OH)$_2$, J=5.74 Hz), 3.50 (t, 4H, N(CH$_2$CH$_2$OH)$_2$), 3.90–4.05 (m, 1H, CH(NH)—), 4.71 (t, 2H, OH, J=5.29 Hz), 6.62 (d, 2H, H$_{arom2+6}$, J=8.98 Hz), 6.82 (d, 2H, H$_{arom3+5}$), 7.88 (d, 1H, NH-G, J=7.90 Hz).

Example 8

Di-t-butyl, N-{4-[N,N-bis(2-mesyloxyethyl)amino]-phenoxycarbonyl}-L-glutamate (8A)

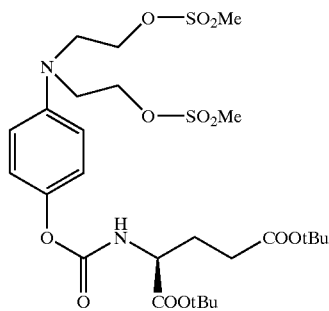

The bis-hydroxy compound 7A (1.73 g, 3.58 mmol) and DMAP (29 mg, 0.24 mmol) were dissolved in dry dichloromethane (50 mL), and cooled in an ice bath under stirring. The cooled solution was treated with a solution of methanesulfonic anhydride (2.7 g, 15.5 mmol) and triethylamine (2.7 mL, 19.3 mmol) in dry dichloromethane (50 mL), and was then allowed to warm up for 18 h. The reaction mixture was diluted with dichloromethane (100 mL) and extracted with 10% aq. citric acid (2×200 mL). The aqueous washings were back-extracted with dichloromethane (50 mL), and the organic fractions pooled, dried (MgSO$_4$) and evaporated to afford 8A as a solid.

$^1$H-NMR (DMSO-d$_6$) $\delta_H$: 1.41 (s, 9H, COO-t-Bu), 1.42 (s, 9H, COO-t-Bu), 1.70–2.00 (2m, 2H, CH$_2$CH(NH)—), 2.28–2.38 (m, 2H, CH$_2$COO), 3.15 (s, 6H, CH$_3$SO$_3$), 3.71 (t, 4H, N(CH$_2$CH$_2$OMes)$_2$, J=5.69 Hz), 3.90–4.05 (m, 1H, CH(NH)—), 4.30 (t, 4H, N(CH$_2$CH$_2$OMes)$_2$), 6.78 (d, 2H, H$_{arom2+6}$, J=9.12 Hz), 6.92 (d, 2H, H$_{arom3+5}$), 7.92 (d, 1H, NH-G, J=7.89 Hz).

Example 9

Di-t-butyl, N-{4-[N,N-bis(2-iodoethyl)amino]-phenoxycarbonyl}-L-glutamate (9A)

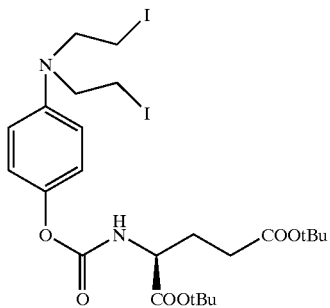

The crude product 8A was dissolved in acetone (100 mL) and treated with NaI (7.1 g, 47.4 mmol). The reaction mixture was refluxed for 4.5 h, then filtered and evaporated. The residue was partitioned between water (200 mL) and dichloromethane (200 mL). The organic layer was washed again with water (2×100 mL). The aqueous layers were combined and back-extracted with dichloromethane (100 mL). The organic fractions were pooled, dried (MgSO$_4$) and evaporated. The residue was purified by column chromatography on silica (starting with hexane: dichloromethane 1:1, then neat dichloromethane) to afford 9A (2.13 g, overall yield 85%) as an orange solid.

$^1$H-NMR (DMSO-d$_6$) δ$_H$: 1.41 (s, 9H, COO-t-Bu), 1.42 (s, 9H, COO-t-Bu), 1.70–2.05 (2m, 2H, CH$_2$CH(NH)—), 2.29–2.39 (m, 2H, CH$_2$COO), 3.31 (t, 4H, N(CH$_2$CH$_2$I)$_2$, J=7.70 Hz), 3.72 (t, 4H, N(CH$_2$CH$_2$I)$_2$), 3.85–4.00 (m, 1H, CH(NH)—), 6.67 (d, 2H, H$_{arom2+6}$, J=9.01 Hz), 6.93 (d, 2H, H$_{arom3+5}$), 7.97 (d, 1H, NH-G, J=7.83 Hz).

Example 10

N-{4-[N,N-bis(2-iodoethyl)amino]-phenoxycarbonyl}-L-glutamic acid (12A)

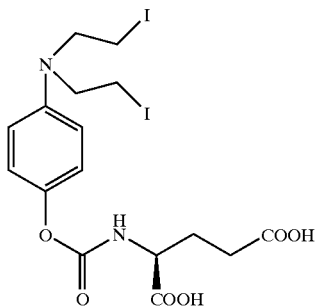

The di-t-butyl ester 9A (1.7 g, 2.42 mmol) was dissolved in TFA (45 mL) and stirred for 55 min at room temperature. The reaction mixture was evaporated 5 times after addition of ethyl acetate (under nitrogen), redissolved in ethyl acetate (5 mL) and toluene (50 mL) was added. The solution was seeded with crystals of 12A. The solution was stored at −20° C. overnight. The formed crystals were recovered by filtration, washed with toluene:ethyl acetate 10:1 and dried to afford 12A (180 mg). The filtrate was concentrated in a rotary evaporator until the first crystals starts to appear, then it was stored overnight at −20° C. A second crop of crystals of 12A (880 mg) was obtained. Repeating the steps described above a third crop (230 mg) was obtained. All 3 crops of crystals were pure by $^1$H-NMR. A total of 1.29 g (90%) of 12A was obtained.

$^1$H-NMR (DMSO-d$_6$) δ$_H$: 1.75–2.10 (2m, 2H, CH$_2$CH(NH)—), 2.36 (t, 2H, CH$_2$COO, J=8.15 Hz), 3.31 (t, 4H, N(CH$_2$CH$_2$I)$_2$, J=7.87 Hz), 3.71 (t, 4H, N(CH$_2$CH$_2$I)$_2$), 3.95–4.05 (m, 1H, CH(NH)—), 6.65 (d, 2H, H$_{arom2+6}$, J=9.08 Hz), 6.94 (d, 2H, H$_{arom3+5}$), 7.94 (d, 1H, NH-G, J=8.10 Hz).

REFERENCES

A number of patents and publications are cited above in order to more fully describe and disclose the invention and the state of the art to which the invention pertains. Full citations for these references are provided below. Each of these references is incorporated herein by reference in its entirety into the present disclosure.

Blakey, D. C; et al. 1996, *Cancer Research*, Vol. 56, pp. 3287–3292.

Burke, P. J., et al., 1994, Published International (PCT) Patent Application No. WO 94/02450.

Corey et al., 1972, *J. Am. Chem. Soc.*, Vol. 94, p. 6190.

Emery, S. C., et al., 1998, Published International (PCT) Patent Application No. WO 98/51787.

Everett, J. L. and Ross, W. C. J., 1949, Aryl-2-halogeno-alkylamines, Part II, *J. Chem. Soc.*, pp. 1972–1983.

Ferenz, C. R., et al., 1989, *Journal of Labelled Compounds & Radiopharmaceuticals*, Vol. 27, pp. 737–751.

Greene, T. W., and Wuts, P. G. M., 1999a, *Protective Groups in Organic Chemistry*, 3rd Edition, pp. 246–293, published by John Wiley & Sons.

Greene, T. W., and Wuts, P. G. M., 1999b, *Protective Groups in Organic Chemistry*, 3rd Edition, pp. 113–148, published by John Wiley & Sons.

Greene, T. W., and Wuts, P. G. M., 1999c, *Protective Groups in Organic Chemistry*, 3rd Edition, pp. 369–428, published by John Wiley & Sons.

Hagermann, H., 1983, Kohlensaure-derivative, in *Houben-Weyl Methoden der Organische Chemie*, Vol. E4, ed. Georg Thieme, published by Verlag, Stuttgart, N.Y.

Hagermann, H., 1985, Organische Schwefel-Verbindungen, in *Houben-Weyl Methoden der Organische Chemie*, Vol. E11, Part 2, pp. 1084–1094, ed. Georg Thieme, published by Verlag, Stuttgart, NewYork Heaton, D. W., et al., 1996, Published International (PCT) Patent Application No. WO 96/20169.

Lalonde et al., *Synthesis*, 1985, pp. 817–845.

March, J., 1992, *Advanced Organic Chemistry*, 4th edition, p. 431, published by John Wiley & Sons.

Periasamy et al., 1979, *Org. Prep. Proceed. Int.*, Vol. 11, pp. 293–311.

Raucher et al., 1985, *Synth. Commun.*, Vol. 15, p. 1025.

Springer, C. J., et al., 1994, Published International (PCT) Patent Application No. WO 94/25429.

Springer, C. J., et al., 1995, *Journal of Medicinal Chemistry*, Vol. 38, pp. 5051–5065.

Springer, C. J., et al., 1996, Published International (PCT) Patent Application No. WO 96/03515.

What is claimed is:

1. A method of synthesis comprising the steps of, in order:

glutamate conjugation (GC), in which a 4-[N,N-bis(2-silyloxyethyl)aminolphenyl haloformate, activated carbonate, or activated carbamate 5, reacts with a glutamate, 15, to give an N-{4-[N,N-bis(2-silyloxyethyl)amino]phenoxycarbonyl}-L-glutamate, 6:

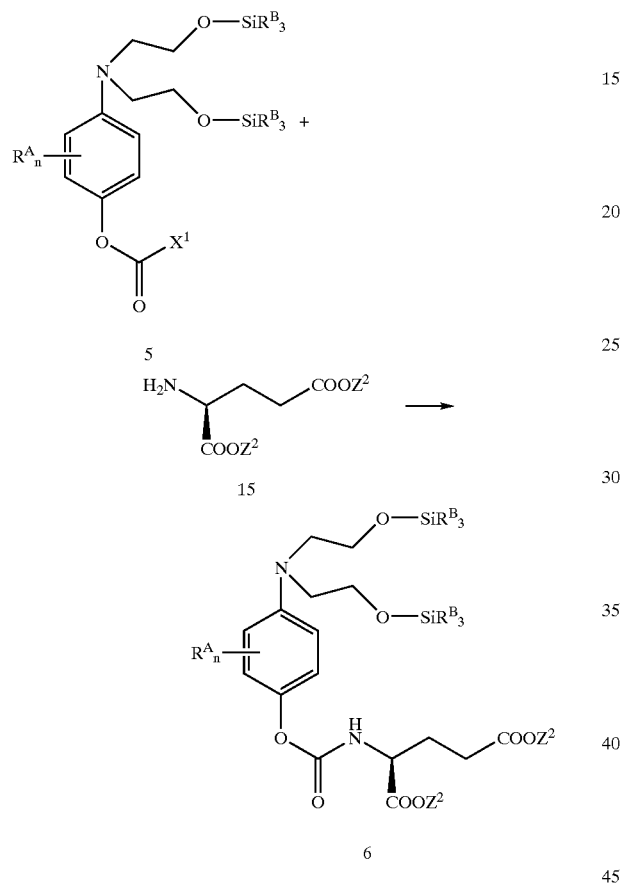

silyloxy deprotection (SD), in which said N-{4-[N,N-bis(2-silyloxyethyl)amino]phenoxy-carbonyl}-L-glutamate, 6, is converted to an N-{4-[N,N-bis(2-hydroxyethyl)amino]phenoxycarbonyl}-L-glutamate, 7:

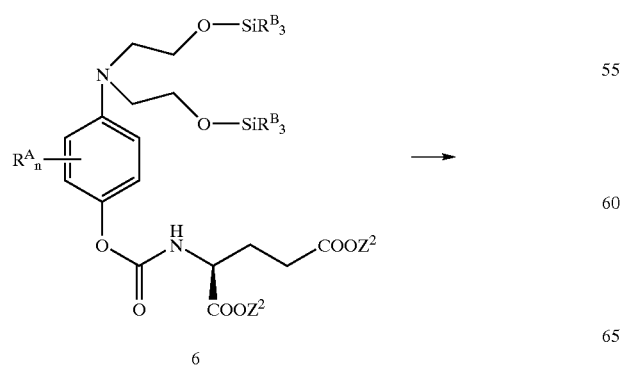

sulfonic esterification (SE), in which said N-{4-[N,N-bis(2-hydroxyethyl)amino]phenoxycarbonyl}-L-glutamate, 7, is converted to an N-{4-[N,N-bis(2-sulfonyloxyethyl)amino]phenoxycarbonyl}-L-glutamate, 8:

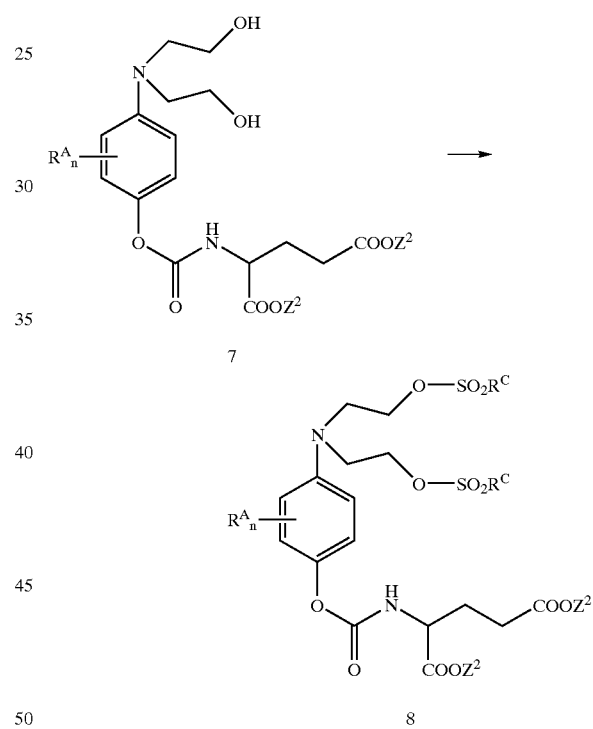

wherein:

$X^1$ is a leaving group;

n is an integer from 0 to 4;

each $R^A$ is independently an aryl substituent;

each $R^B$ is a silyl substituent, and is independently $C_{1-7}$alkyl, $C_{3-20}$heterocyclyl, or $C_{5-20}$aryl, and is optionally substituted;

each $R^C$ is a sulfonic substituent, and is independently $C_{1-7}$alkyl, $C_{3-20}$heterocyclyl, or $C_{5-20}$aryl, and is optionally substituted; and, each $Z^2$ is independently a carboxylic acid protecting group.

2. A method according to claim 1, further comprising, following the step of sulfonic esterification (SE), the additional step of:

halogenation (HL), in which said N-{4-[N,N-bis(2-sulfonyloxethyl)amino]phenoxycarbonyl}-L-glutamate, 8, is converted to an N-{4-[N,N-bis(2-haloethyl)amino]phenoxycarbonyl}-L-glutamate, 9:

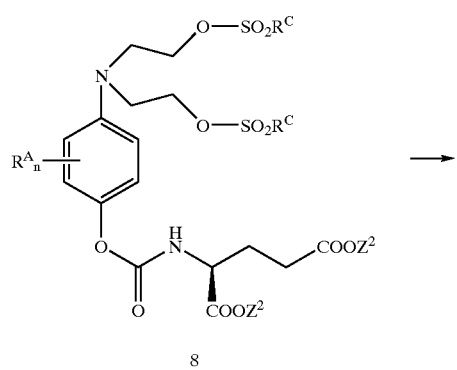

8

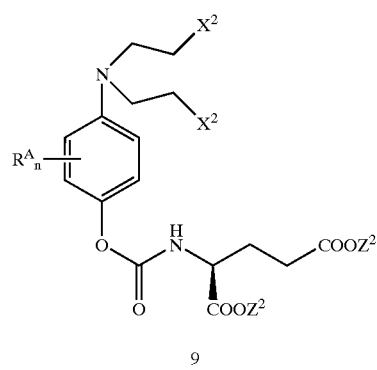

9 wherein each $X^2$ is independently —F, —Cl, —Br, —I.

3. A method according to claim 1, further comprising, following the step of sulfonic esterification (SE), the additional step of:

halogenation (HL), in which said N-{4-[N,N-bis(2-sulfonyloxyethyl)amino]phenoxycarbonyl}-L-glutamate, 8, is converted to an N-{4-[N-(2-sulfonyloxyethyl), N-(2-haloethyl)amino]phenoxycarbonyl}-L-glutamate, 10:

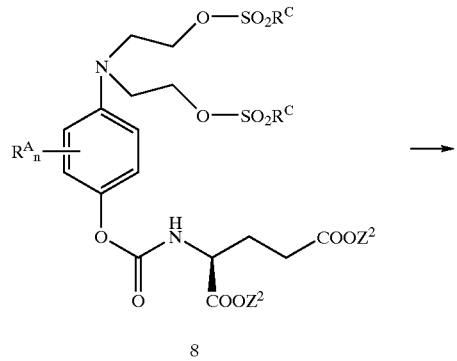

8

-continued

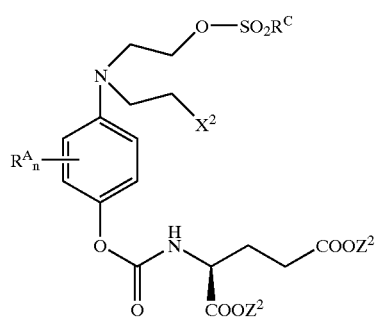

10 wherein each $X^2$ is independently —F, —Cl, —Br, —I.

4. A method according to claim 1, further comprising, following the step of sulfonic esterification (SE), the additional step of:

glutamate deprotection (GD), in which said N-{4-[N,N-bis(2-sulfonyloxyethyl)amino]phenoxycarbonyl}-L-glutamate, 8, is converted to an N-{4-[N,N-bis(2-sulfonyloxyethyl)amino]phenoxycarbonyl}-L-glutamic acid, 11:

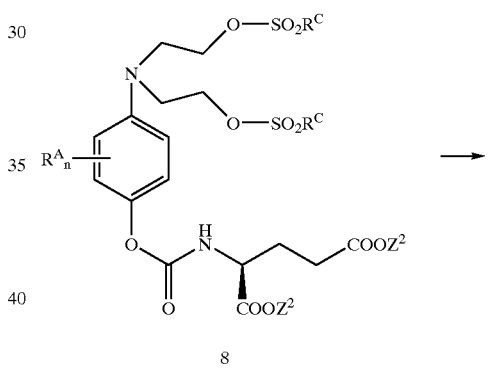

8

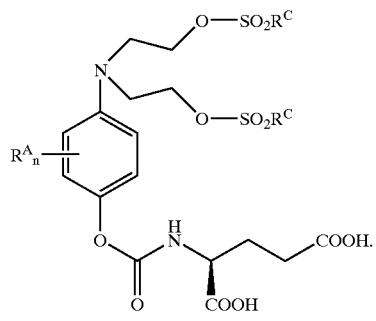

11

5. A method according to claim 2, further comprising, following the step of halogenation (HL), the additional step of:

glutamate deprotection (GD), in which said N-{4-[N,N-bis(2-haloethyl)amino]phenoxycarbonyl}-L-glutamate, 9, is converted to an N-{4-[N,N-bis(2-haolethyl)amino]phenoxycarbonyl}-L-glutamic acid, 12;

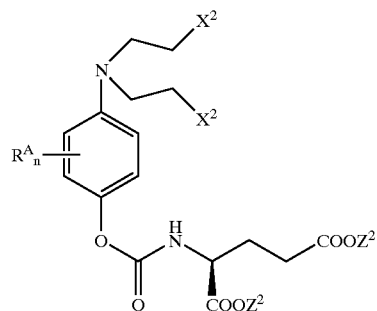

9

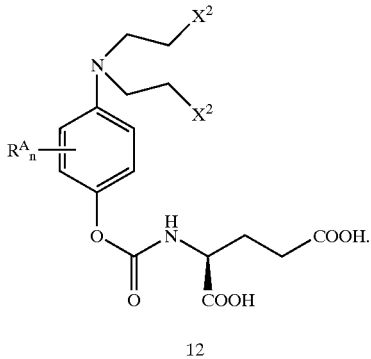

12

6. A method according to claim 3, further comprising, following the step of halogenation (HL), the additional step of:

glutamate deprotection (GD), in which said N-{4-[N-(2-sulfonyloxyethyl), N-(2-haloethyl)amino]phenoxycarbonyl}-L-glutamate, 10, is converted to an N-{4[N-(2-sulfonyloxyethyl), N-(2-haloethyl)amino]phenoxycarbonyl}-L-glutamic acid, 13:

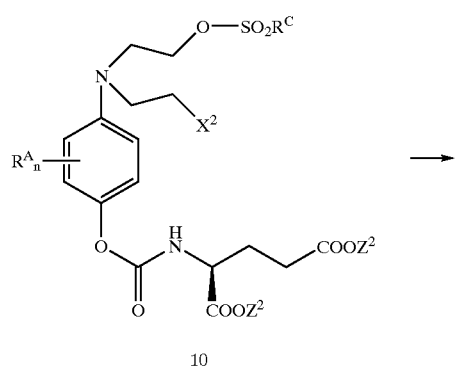

10

-continued

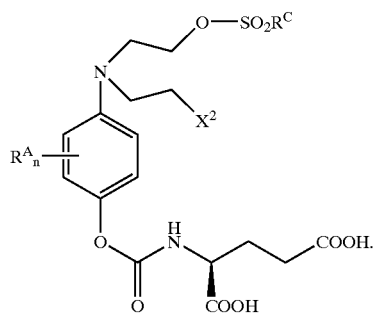

13

7. A method according to claim 1, further comprising, preceding the step of glutamate conjugation (GC), the additional step of:

activation (AC), in which a 4-[N,N-bis(2-silyloxyethyl)amino]phenol, 4, is converted to said 4-[N,N-bis(2-silyloxyethyl)amino]phenyl haloformate, activated carbonate, or activated carbamate 5:

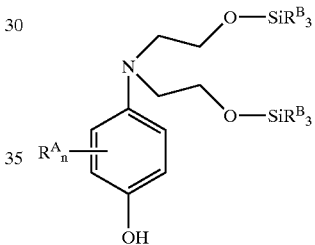

4

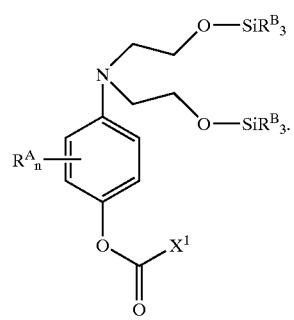

5

8. A method according to claim 7, further comprising, preceding the step of activation (AC), the additional steps of:

silyloxy protection (SP), in which a 4-(protected hydroxy)-N,N-bis(2-hydroxyethyl)anliline, 2, is converted to a 4-(protected hydroxy)-N,N-bis(2-silyloxyethyl)aniline, 3:

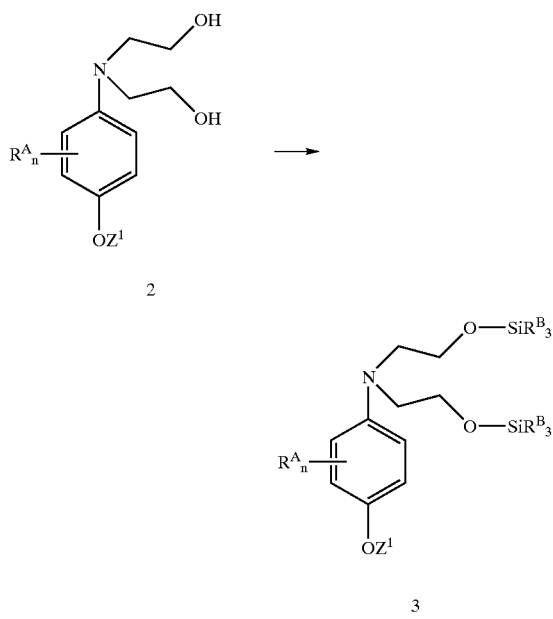

2

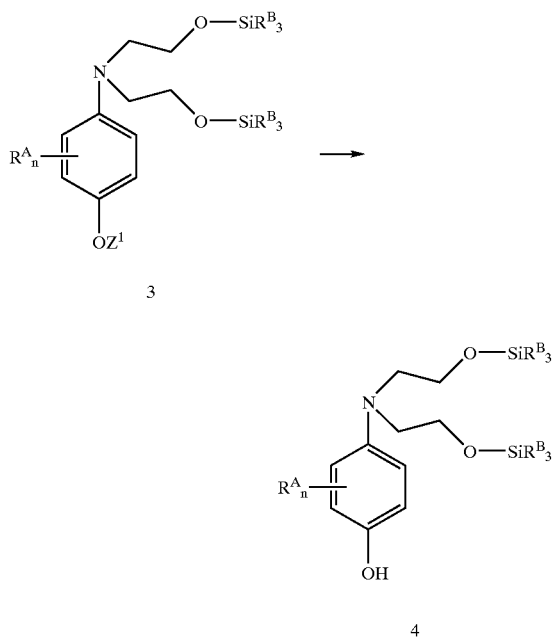

3 phenolic deprotection (PD), in which said 4-(protected hydroxy)-N,N-bis(2-silyloxyethyl)aniline, 3, is converted to said 4-N,N-bis(2-silyloxyethyl)amino]phenol, 4:

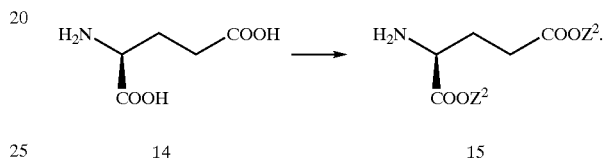

3

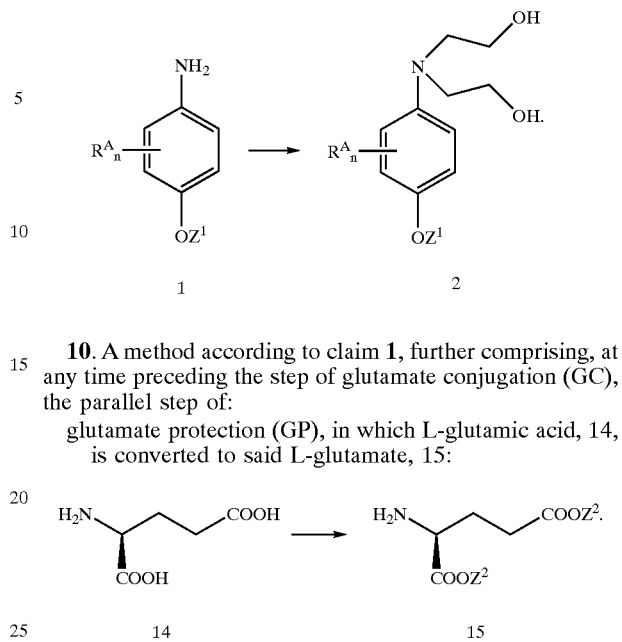

4 wherein $Z^1$ is a phenol protecting group.

9. A method according to claim 8, further comprising, preceding the step of silyloxy protection (SP), the additional step of:

amine substitution (AS), in which a 4-(protected hydroxy)-aniline, 1, is converted to said 4-(protected hydroxy)-N,N-bis(2-hydroxyethyl)aniline, 2:

10. A method according to claim 1, further comprising, at any time preceding the step of glutamate conjugation (GC), the parallel step of:

glutamate protection (GP), in which L-glutamic acid, 14, is converted to said L-glutamate, 15:

11. A method according to claim 1, wherein said glutamate conjugation (GC) step is achieved by reaction in the presence of a base.

12. A method according to claim 1, wherein said glutamate conjugation (GC) step is achieved by reaction in the presence of the base triethylamine.

13. A method according to claim 1, wherein said silyloxy deprotection (SD) step is achieved by reaction with triethylamine trihydrofluoride ($NEt_3 \cdot 3HF$).

14. A method according to claim 1, wherein said sulfonic esterification (SE) step is achieved by reaction with a sulfonic anhydride, $(R^CSO_2)_2O$.

15. A method according to claim 1, wherein said sulfonic esterification (SE) step is achieved by reaction with a sulfonic anhydride, $(R^CSO_2)_2O$, in the presence of a base.

16. A method according to claim 1, wherein said sulfonic esterification (SE) step is achieved by reaction with a sulfonic anhydride, $(R^CSO_2)_2O$, in the presence of one or both of triethylamine and 4-dimethylaminopyridine.

17. A method according to claim 14, wherein said sulfonic anhydride is methanesulfonic anhydride, $(MeSO_2)_2O$.

18. A method according to claim 2, wherein said halogenation (HL) step is achieved by reaction with an alkaline halide.

19. A method according to claim 18, wherein said alkaline halide is sodium iodide.

20. A method according to claim 4, wherein said glutamate deprotection (GD) step is achieved by reaction with acid.

21. A method according to claim 4, wherein said glutamate deprotection (GD) step is achieved by reaction with trifluoroacetic acid.

22. A method according to claim 7, wherein said activation (AC) step is achieved by reaction with a carbonyl halide, $X^1C(=O)X^1$.

23. A method according to claim 7, wherein said activation (AC) step is achieved by reaction with a carbonyl halide, $X^1C(=O)X^1$ in the presence of a base.

24. A method according to claim 7, wherein said activation (AC) step is achieved by reaction with a carbonyl halide, $X^1C(=O)X^1$ in the presence of the base triethylamine.

25. A method according to claim 22, wherein said carbonyl halide is phosgene, ClC(=O)Cl.

26. A method according to claim 8, wherein said silyloxy protection (SP) step is achieved by reaction with the corresponding halosilane, $SiR^B_3X$.

27. A method according to claim 8, wherein said silyloxy protection (SP) step is achieved by reaction with the corresponding chlorosilane, $SiR^B_3Cl$.

28. A method according to claim 8, wherein said silyloxy protection (SP) step is achieved by reaction with the corresponding halosilane, $SiR^B_3X$, in the presence of a base.

29. A method according to claim 8, wherein said silyloxy protection (SP) step is achieved by reaction with the corresponding halosilane, $SiR^B_3X$, in the presence of the base imidazole.

30. A method according to claim 8, wherein said phenolic deprotection (PD) step is achieved by treatment with hydrogen gas and a palladium/carbon catalyst.

31. A method according to claim 9, wherein said amine substitution (AS) step is achieved by treatment with ethylene oxide.

32. A method according to claim 9, wherein said amine substitution (AS) step is achieved by treatment with ethylene oxide in acetic acid, in the presence of a base.

33. A method according to claim 9, wherein said amine substitution (AS) step is achieved by treatment with ethylene oxide in acetic acid, in the presence of the base triethylamine.

34. A method according to claim 10, wherein said glutamate protection (GP) step is achieved by reaction with isobutylene in the presence of sulfuric acid.

35. A method according to claim 1, wherein $X^1$ is —F, —Cl, —Br, p-nitrophenoxy, pentafluorophenoxy, succinimidyloxy, or imidazolyl.

36. A method according to claim 1, wherein $X^1$ is —F, —Cl, or —Br.

37. A method according to claim 1, wherein $X^1$ is —Cl.

38. A method according to claim 1, wherein $X^1$ is p-nitrophenoxy, pentafluorophenoxy, succinimidyloxy.

39. A method according to claim 1, wherein $X^1$ is imidazolyl.

40. A method according to claim 1, wherein each $R^A$ is independently an aryl substituent selected from: halo; ether; thioether; acyl; ester; amido; disubstituted amino; cyano; nitro; and, $C_{1-7}$alkyl.

41. A method according to claim 1, wherein n is 0.

42. A method according to claim 1, wherein each $R^B$ is independently —Me, -Et, -nPr, -iPr, -nBu, -sBu, -iBu, -tBu, or —Ph.

43. A method according to claim 1, wherein each $—SiR^B_3$ group is independently $—Si(Me)_3$, $—Si(Et)_3$, $—Si(iPr)_3$, $—Si(tBu)(Me)_2$, or $—Si(Ph)_h(tBu)$.

44. A method according to claim 1, wherein each 13 $SiR^B_3$ groups is $—Si(tBu)(Me)_2$.

45. A method according to claim 1, wherein each $R^C$ is $C_{1-7}$alkyl or $C_{5-20}$aryl, and is optionally substituted.

46. A method according to claim 1, wherein each $R^C$ is —Me.

47. A method according to claim 1, wherein each $R^C$ is phenyl or substituted phenyl.

48. A method according to claim 1, wherein each $Z^2$ is independently t-butyl, allyl, or benzyl.

49. A method according to claim 1, wherein each $Z^2$ is t-butyl.

50. A method according to claim 2, wherein $X^2$ is —Cl, —Br, or —I.

51. A method according to claim 2, wherein $X^2$ is —Cl.

52. A method according to claim 2, wherein $X^2$ is —I.

53. A method according to claim 8, wherein $Z^1$ is benzyl or allyl.

54. A method according to claim 8, wherein $Z^1$ is benzyl.

* * * * *